(12) United States Patent
Zhou et al.

(10) Patent No.: US 8,808,530 B2
(45) Date of Patent: Aug. 19, 2014

(54) METHOD AND APPARATUS FOR ELECTROCATALYTIC AMPLIFICATION ON PRE-OXIDIZED MEASURING ELECTRODE

(75) Inventors: Hongjun Zhou, Austin, TX (US); Allen J. Bard, Austin, TX (US); Fu-Ren F. Fan, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 47 days.

(21) Appl. No.: 13/212,022

(22) Filed: Aug. 17, 2011

(65) Prior Publication Data

US 2012/0043225 A1    Feb. 23, 2012

Related U.S. Application Data

(60) Provisional application No. 61/375,176, filed on Aug. 19, 2010.

(51) Int. Cl.
*G01F 1/64*   (2006.01)
*G01N 27/416* (2006.01)

(52) U.S. Cl.
CPC .................................. *G01N 27/416* (2013.01)
USPC .......................................... 205/775; 204/400

(58) Field of Classification Search
USPC ................... 204/400–432; 205/775
See application file for complete search history.

(56) References Cited

U.S. PATENT DOCUMENTS

| | | | |
|---|---|---|---|
| 6,537,498 B1 | 3/2003 | Lewis et al. | |
| 6,972,173 B2 | 12/2005 | Su et al. | |
| 7,741,033 B2 | 6/2010 | Kelley et al. | |
| 2009/0065371 A1* | 3/2009 | Xiao et al. | 205/790.5 |

FOREIGN PATENT DOCUMENTS

| | | | |
|---|---|---|---|
| WO | WO2009/126249 | * | 10/2009 |
| WO | 2012024439 | | 2/2012 |

OTHER PUBLICATIONS

Jwa-Min Nam, et al.; "Nanoparticle-Based Bio-Bar Codes for the Ultrasensitive Detection of Proteins", Science 301, 1884 (Sep. 26, 2003).
Celikkan, et al; "The investigation of the electrooxidation of sodium borohydride on various metal electrodes in aqueous basic solutions", International Journal of Hydrogen Energy 32 (2007), pp. 588-593.
International Search Report and Written Opinion for PCT/US2011/048142 dated Mar. 20, 2012.
Polsky, Ronen, et al., "Nucleic Acid-Functionalized Pt Nanoparticles: Catalytic Labels for the Amplified Electrochemical Detection of Biomolecules," Analytical Chemistry, vol. 78, No. 7, pp. 2268-2271 (2006).

(Continued)

*Primary Examiner* — Bach Dinh
(74) *Attorney, Agent, or Firm* — Chainey P. Singleton; Edwin S. Flores; Chalker Flores, LLP

(57) ABSTRACT

The present invention includes methods and compositions having at least one nanoparticle for analyzing a chemical analyte. The device includes an electrochemical cell connected to a measuring apparatus, wherein the electrochemical cell comprises a container and at least one electrode comprising a surface modification; a solution within the container comprising one or more chemical analytes and one or more metal nanoparticles in the solution, wherein one or more electrocatalytic properties are generated by the one or more metal nanoparticles at the at least one electrode and the contact of individual nanoparticles can be measured.

23 Claims, 18 Drawing Sheets

(56) References Cited

OTHER PUBLICATIONS

Celikkan, Huseyin, et al., "The Investigation of the Electrooxidation of Sodium Borohydride on Various Metal Electrodes in Aqueous Basic Solutions," Hydrogen Energy, (2007), 32:588-893.

Conway, B.E., et al., "Independence of Formation and Reduction of Monolayer Surface Oxide on Pt from Presence of Thicker Phase-Oxide Layers," J. Electroanal. Chem., (1991), 297:435-443.

Jain, Prashant K., et al., "Au Nanoparticles Target Cancer," NanoToday, Feb. 2007, vol. 2, No. 1, pp. 18-29.

Liu, Bin Hong, et al., "Anodic Oxidation of Alkali Borohydrides Catalyzed by Nickel," Journal of the Electrochemical Society, (2003), 150(3):A398-A402.

Liu, Bin Hong, et al., "Concentration Ratio of [OH_]/[BH_4]: A Controlling Factor for the Fuel Efficiency of Borohydride Electro-Oxidation," International Journal of Hydrogen Energy, (2009), 34:9436-9443.

Nam, Jwa-Min, et al., "Nanoparticle-Based Bio-Bar Codes for the Ultrasensitive Detection of Proteins," Science, Sep. 26, 2003, vol. 301, No. 5641, vol. 30, No. 5641, pp. 1884-1886.

Qian, Lei, et al., "Layer-by-Layer Assembled Multilayer Films of Redox Polymers for Electrocatalytic Oxidation of Ascorbic Acid," Sensors and Actuators, (2005), 107:303-310.

Santos, D.M.F., et al., "Chronopotentiometric Investigation of Borohydride Oxidation at a Gold Electrode," Journal of the Electrochemical Society, (2010), 157(1):F16-F21.

Xiao, Xiaoyin, et al., "Observing Single Nanoparticle Collisions at an Ultramicroelectrode by Electrocatalytic Amplification," JACS, Jul. 14, 2007, 129:9610-9612.

Xiao, Xiaoyin, et al., "Current Transients in Single Nanoparticle Collision Events," JACS, (2008), 130:16669-16677.

Xiao, Xiaoyin, et al., "Single Nanoparticle Electrocatalysis: Effect of Monolayers on Particle and Electrode on Electron Transfer," J. Phys. Chem., (2009), 113:14978-14982.

Yang, J., et al., "Size Effect in Thiol and Amine Binding to Small Pt Nanoparticles," Analytica Chimica Acta, (2006), 571:206-210.

\* cited by examiner

METHOD AND APPARATUS FOR ELECTROCATALYTIC AMPLIFICATION ON PRE-OXIDIZED MEASURING ELECTRODE

CROSS-REFERENCE TO RELATED APPLICATIONS

This application claims priority to U.S. Provisional Application Ser. No. 61/375,176, filed Aug. 19, 2010, the contents of which is incorporated by reference herein in its entirety.

STATEMENT OF FEDERALLY FUNDED RESEARCH

This invention was made with U.S. Government support under Contract No. CHE-0808927 by the National Science Foundation. The government has certain rights in this invention.

TECHNICAL FIELD OF THE INVENTION

The present invention relates in general to the field of nanoparticles; and in particular, the present invention relates to instruments, methods and reagents for amplifying a signal from a catalytic reaction using metal nanoparticles.

INCORPORATION-BY-REFERENCE OF MATERIALS FILED ON COMPACT DISC

None.

BACKGROUND OF THE INVENTION

Without limiting the scope of the invention, its background is described in connection with nanoparticles. The physical properties (e.g., high surface-to-volume ratio, elevated surface energy, increased ductility after pressure loading, higher hardness, larger specific heat and the like) of nanoparticles have led to increased applications in the material-directed industry and material science. For example, a variety of metal nanoparticles have been used to catalyze numerous reactions.

The size of nanoparticles range from the 0.5 to 100 nm and the electronic energy band configuration is a size-dependent property, which in turn affect the physical and chemical properties. A fundamental distinction between nanoparticles and their bulk materials is that the fraction of surface atoms and the radius of curvature of the surface are comparable with the lattice constant. As a result, the nanostructured catalysts have a higher catalytic activity of as compared with their analogues based on bulk materials. The methods of forming nanoparticles are known to the skilled artisan and include formation by combining atoms (or more complex radicals and molecules) and by dispersion of bulk materials, e.g., thermal evaporation, ion sputtering, reduction from solution, reduction in microemulsions and condensation.

Colloidal particles have been used in sensing arrays for chemical sensors analyte by detection of analytes. For example, U.S. Pat. No. 6,537,498 entitled, "Colloidal Particles Used in Sensing Arrays" discloses chemical sensors for detecting analytes in fluids having a plurality of alternating nonconductive regions and conductive regions of conductive nanoparticle materials.

Another example includes U.S. Pat. No. 6,972,173 entitled, "Methods to Increase Nucleotide Signals by Raman Scattering" teaches methods and apparatus relating to nucleic acid sequencing by enhanced Raman spectroscopy using nucleotides covalently linked to silver or gold nanoparticles.

Electrocatalysis at nanoparticles, for analytical purposes, has been described in the art; however, such descriptions involve large numbers of nanoparticles, at least hundreds of thousands, as monolayer or near monolayer films on electrode surfaces

SUMMARY OF THE INVENTION

The present invention provides a device having at least one nanoparticle for analyzing a chemical analyte. The device includes an electrochemical cell connected to a measuring apparatus, wherein the electrochemical cell comprises a container and at least one electrode comprising a surface modification; a solution within the container comprising one or more chemical analytes and one or more metal nanoparticles in the solution, wherein one or more electrocatalytic properties are generated by the one or more metal nanoparticles at the at least one electrode and the contact of individual nanoparticles can be measured.

The present invention provides an electrochemical cell to analyze a sample by electrocatalytic amplification using one or more nanoparticles having one or more electrodes positioned to communicate with a sample housed within a sample chamber, wherein the one or more electrodes comprise a surface coating; one or more nanoparticles deposited within the sample chamber, wherein the one or more nanoparticles interact with the sample to generate one or more electrocatalytic properties; and a detector in communication with the one or more electrodes to detect the one or more electrocatalytic properties wherein the detector can detect individual nanoparticles contacting the electrode by measuring at least one of electrical current, potential, charge, impedance, light, and color.

The present invention provides a method of analyzing a sample using nanoparticle collision amplification at a surface modified electrode by providing a sample chamber having at least 2 electrodes, wherein one or more of the at least 2 electrodes comprise a surface modification; combining one or more metal nanoparticles with a liquid sample within the sample chamber; detecting an oxidation or reduction reaction between the one or more nanoparticles and at least one of the at least 2 electrodes, wherein the detector can detect individual nanoparticles contacting the electrode by measuring at least one of electrical current, potential, charge, impedance, light, and color; and observing one or more electrocatalytic properties generated by the oxidation or reduction reaction.

The skilled artisan can detect a single nanoparticle collision event with an ultramicroelectrode or nanoelectrode through a novel amplification scheme. The single particle collision event produces a current-time transient that can have highly sensitive analytical implications. As a basic requirement of this protocol, the nanoparticle should possess much higher catalytic activity than the measuring electrode itself, e.g., Pt NPs at Au, or carbon electrodes for hydrazine oxidation and IrO$_x$ NPs at Pt or Au electrode for water oxidation. This greatly limits further application of this technology. However, through surface modification of the electrode, this limitation can be overcome. For example, the oxidation of NaBH$_4$ occurs rapidly at a Pt electrode surface, but became sluggish after electrochemically growing a thin layer of oxide. As a result, the collision of the less electro-catalytic metal (e.g. Au) nanoparticle at this oxide coated electrode surface produces a unique current spike which correlates with the particle size, the particle residence time, and the nature of the particle interaction with the electrode surface and the surface treatment of the measuring electrodes.

This technology of tuning the electrode surface or manipulating its physicochemical properties greatly increases the flexibility in the choices of nanoparticles and electrodes, which would help in achieving deeper understanding of collision process and in further applications in biotechnology and single molecule detection. For example, the synthesis of Au nanoparticles with different shapes, sizes and stabilizing agent has widely been reported. Also, Au nanoparticles have been widely applied in bio-nanotechnology due to its unique optical properties and biocompatibility.

And this electrochemical amplification technology can be used to determine nanoparticle size distributions, to examine porosity of surface films and as a very sensitive electroanalytical technique. It should have applications in nanotechnology and biotechnology as a simple, low-cost, rapid, and ultra high-sensitivity analytical method by exploring and detecting single binding events between biomolecules (DNA hybridization, interactions between protein-DNA, antibody-antigen, and protein-small molecules). Single molecule detection levels are possible.

The present invention provides the electrochemically catalytic amplification of nanoparticles, which is unique and at very high orders of magnitude. Such large amplification factors have allowed observation of single particle collision event. By studying individual collision event, there is no question that the multiple processes involved in such a single event can be further explored and analyzed, such as frequency-related particle concentration and size of electrode, amplitude-related particle size and the nature of particle interaction with the electrode surfaces, and so on.

Catalytic amplification using a monolayer of nanoparticles has already been widely demonstrated in biosensors and biotechnology. Different from our previous platinum and $IrO_x$ nanoparticle collision experiment, the present invention provides catalytic amplification of a single gold nanoparticle collision through a surface modification of a platinum electrode and use it to study the single event of a particle interacting with the electrode surfaces at a much shorter residence time. This new technology allows us to observe collisions of a nanoparticle at an electro-active electrode, which is otherwise impractical, by tuning the properties of the measuring electrode.

Although SEM, TEM and light scattering are widely used to study particle size distributions, the present invention has the potential to determine the size distribution and in many cases the chemical identity of the nanoparticles. Fluorescence microscopy, surface plasmon resonance and enhanced Raman and vibrational spectroscopy are very useful in biotechnology to detect and screen the binding between biomolecules. This electrochemical technique can detect such interactions at the single nanoparticle level and with much less expensive, simpler, and portable apparatus. The analysis of biomolecules at low concentrations, the determination of particle size distributions, the determination of the porosity of surface films and the electrode materials, the study of charge transfer kinetics between nanoparticles and electrodes, between different materials and between different distances. Easy and fast operation, low cost, high sensitivity, high amplification factors, selective to both nanoparticles and electrode surfaces. The present invention provides gold nanoparticles, which have been studied more intensively than other materials and are very versatile in terms of modification and synthesis. Adsorption of other species in the matrix on the electrodes can interfere by causing additional background current or passivating the electrode. The problem can be overcome by using clean electrochemical systems (cell and electrolyte), sample pretreatment, precondition of electrodes and modifying the supporting electrode surfaces.

The present invention provides a method to detect a single nanoparticle collision event with ultramicroelectrodes or nanoelectrodes. We characterized a single particle collision event with the current-time transient produced in particle-catalyzed reaction of indicators. The indicator reactions we selected are very specific to either the nature of the nanoparticles or the supporting electrode surfaces, or whose reactants are presented in electrolyte with much higher concentration and much larger diffusion coefficient than the nanoparticles. By catalytic reactions we can achieve very large amplification factors in the current. As a fundamental requirement of this technique, the electrode should be inert or much less electro-active than nanoparticles. The surface modification of the electrode surface can turn active electrodes into inert ones, which allows the usage of less electro-active nanoparticles. As an example, we studied the oxidation of sodium borohydride (in basic solution) that is significant at platinum surfaces, but negligible at platinum oxide surfaces. In the test solution, gold nanoparticles have catalytic properties while the platinum electrode becomes inert due to the formation of surface oxide layer at a certain potential window. As a result, every collision of a gold particle at the electrode surface produces a unique current-time profile, which correlates with the particle size, the particle residence time, and the nature of the particle interaction with the electrode surface and the size of measuring electrode. By using appropriate binding reactions, e.g. antibody-antigen or DNA, one can detect species at the single molecule or few molecules level. Easy and fast operation, low cost, high sensitivity, high amplification factors, selective to both nanoparticles and electrode surfaces and high signal-to-noise ratio can be obtained with nanoelectrodes.

After growing a thin layer of oxide ($PtO_x$) by anodization of a Pt electrode, it changed from catalytically active for electrochemical $NaBH_4$ oxidation into an inactive electrode. When held at a potential where the oxide film was maintained, collisions of individual Au nanoparticles (NPs) that catalyzed $NaBH_4$ oxidation were successfully observed as discrete current pulses (spikes or blips) for each NP interaction with the modified Pt electrode via amplification from $NaBH_4$ oxidation. The current response is affected by NP concentration and the applied potential.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
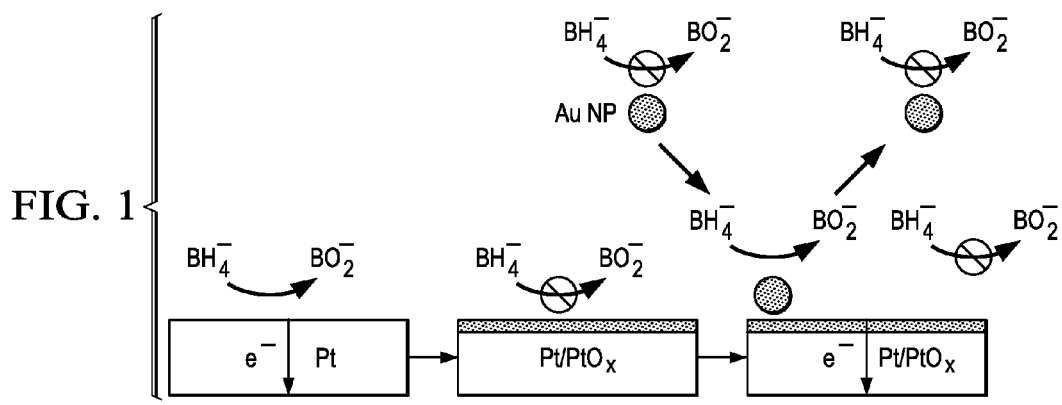
FIG. 1 is a schematic of a single Au nanoparticle collision event on a $Pt/PtO_x$ UME.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "linked" or "linking" refers to an association between two moieties. The association can be a covalent bond. The association can be a non-covalent bond, including but not limited to, ionic interactions, hydrogen bonds, and van der Waals forces. Exemplary non-covalent bonds include hybridization between complementary oligonucleotides and/or polynucleotides, biotin/streptavidin interactions, and antibody/antigen interactions.

As used herein, the term "nanoparticle" as used herein refers to an individual nanoparticle, unless otherwise indicated. Nanoparticles, as disclosed herein, are materials with dimensions at the nanoscale, which ranges from about 0.5 nm to about 100 nm. According to the present disclosure, nanoparticles may comprise metals as well as nonmetals, and may be coated or capped. The term "nanoparticle" according to the invention does not encompass biological compounds.

As used herein, the term "electrode" as used herein refers to an electrically conductive measuring part of an electrochemical cell. As disclosed herein, the electrode is a poor electrocatalyst for the redox reactant and is sufficiently conductive to enable charge transfer to contacting nanoparticles.

As used herein, the term "contact" as used herein refers to two objects being within the tunneling distance of one another. Within this distance, charge transfer can occur.

As used herein, the term "redox reactant" as used herein, refers to a material in an electrochemical cell, distinct from the nanoparticle and the electrode that is capable of undergoing a reduction or oxidation reaction.

As used herein, the term "linked" or "linking" refers to an association between two moieties. The association can be a covalent bond. The association can be a non-covalent bond, including but not limited to, ionic interactions, hydrogen bonds, and van der Waals forces. Exemplary non-covalent bonds include hybridization between complementary oligonucleotides and/or polynucleotides, biotin/streptavidin interactions, and antibody/antigen interactions.

As used herein, the term "electrocatalyst" as used herein refers to a material that is capable of amplifying the rate of electrochemical oxidation or reduction of a redox reactant. In at least one embodiment, contact between a nanoparticle and an electrode enables charge transfer between the nanoparticle and the electrode and enables the nanoparticle to become an electrocatalyst for the redox reactant.

As used herein, the term "trace amount" as used herein means that a material is present, if at all, in an amount that cannot measurably contribute to an electrocatalytic reaction.

As used herein the term "redox reactant" as used herein, refers to a material in an electrochemical cell, distinct from the nanoparticle and the electrode that is capable of undergoing a reduction or oxidation reaction. In addition, nanoparticles that contact the electrode may become an electrocatalyst for a redox reactant in the solution. The redox reactant may be found in solution that contains charge carriers such as Na$^+$, K$^+$, Ca$^{2+}$, Mg$^{2+}$, Cl$^-$, PO$_4^{3-}$, NH$_4^+$. The solution can contain pH buffers. The solution can contain other compounds, such as surfactants, sugars, fats, proteins, etc. As used herein the term "electrocatalyst" as used herein refers to a material that is capable of amplifying the rate of electrochemical oxidation or reduction of a redox reactant. In at least one embodiment, contact between a nanoparticle and an electrode enables charge transfer between the nanoparticle and the electrode and enables the nanoparticle to become an electrocatalyst for the redox reactant. For a particular embodiment, the redox reactant can be selected in light of the nanoparticle and the electrode so that the nanoparticle acts as an electrocatalyst for the redox reactant, while the electrode has little to no electrocatalytic ability for the redox reactant. Exemplary redox reactants include methanol, hydrogen peroxide, and proton with platinum-containing nanoparticles and carbon-containing electrodes. Other exemplary redox reactants include hydrogen peroxide, proton, hydrazine, and oxygen with platinum-containing nanoparticles and gold-containing electrodes. Other exemplary redox reactants include tripropylamine with carbon-containing nanoparticles and a nickel-containing electrode.

The present invention provides methods based on the large current amplification factor involved in a rapid electrocatalytic reaction of a species in single particle collision events.

The reaction of the species at a relatively high concentration in solution at the nanoparticle does not occur at the conductive, but not catalytic, measuring ultramicroelectrode (UME). The skilled artisan will recognize that the measuring microelectrode surface can be treated to decrease the activity for a particular electrode reaction, for example by forming an oxide film or adsorbing certain compounds. The electrode can also be treated to promote the adsorption or sticking of the catalytic particle and this can provide the basis of various analytical schemes.

The present inventors described a scheme to observe the currents caused by collisions of individual NPs at an electrode by electrocatalytic amplification. The protocol mainly involves three components: (1) choice of an inner sphere heterogeneous electron transfer reaction, whose reaction kinetics strongly depend on the electrode material (e.g. proton reduction or hydrazine oxidation); (2) a colloidal solution of a low concentration (~pM) of NPs that are electrocatalytic for this inner sphere reaction; (3) an inert conductive ultramicroelectrode (UME) which, at the applied potential, shows essentially no electrocatalytic effect on this reaction.

The selection of electrode material is critical in observing NP collisions. To obtain a negligible current from the electrode at the applied potential, its electrocatalysis for the chosen reaction should be small; typically C or Au electrodes have been used. The detecting electrode must be a UME (radius about nm to μm) to minimize collisions of more than one particle at a time and to obtain a good signal/noise ratio, since the current that results from the collision of a single NP is very small. The NP must be a good electrocatalyst for the reaction, and Pt NPs have usually been used. The NP must interact with the electrode surface so that the residence times of NPs at the electrode surface are sufficiently long to allow the current from a single NP collision to be detected. Indeed in the previous studies, the particles stuck to the electrode, so each showed a characteristic current step and an overall staircase response.

FIG. 1 is a schematic of a single Au nanoparticle collision event on a Pt/PtO$_x$ UME. An active Pt electrode was changed into one with an inactive surface by simply growing a thin layer of oxide via anodization. The oxide layer inhibited the inner sphere reaction on Pt surface, but was still able to allow electron tunneling, e.g. to NPs in solution, to take place. NaBH$_4$ was used as a heterogeneous inner sphere reactant. Borohydride oxidation (E$^0$=−1.24 vs NHE), as many other multi-electron transfer reactions, depends strongly on the electrode material. To suppress the hydrolysis of NaBH$_4$, 10 mM NaBH$_4$ was dissolved in 0.1 M NaOH. As shown in FIG. 3, the oxidation of NaBH$_4$ starts at negative potentials at both Au and Pt UMEs. The oxidation at the Pt UME occurs more easily (i.e., shows a negative shift in onset potential by about 0.3 V) compared to the Au UME (region I). However, injecting Pt NPs and recording the current at an Au UME, following previous studies on hydrazine oxidation, only resulted in steady current increases with no distinguishable current steps from single NP collisions.

Figure 2:
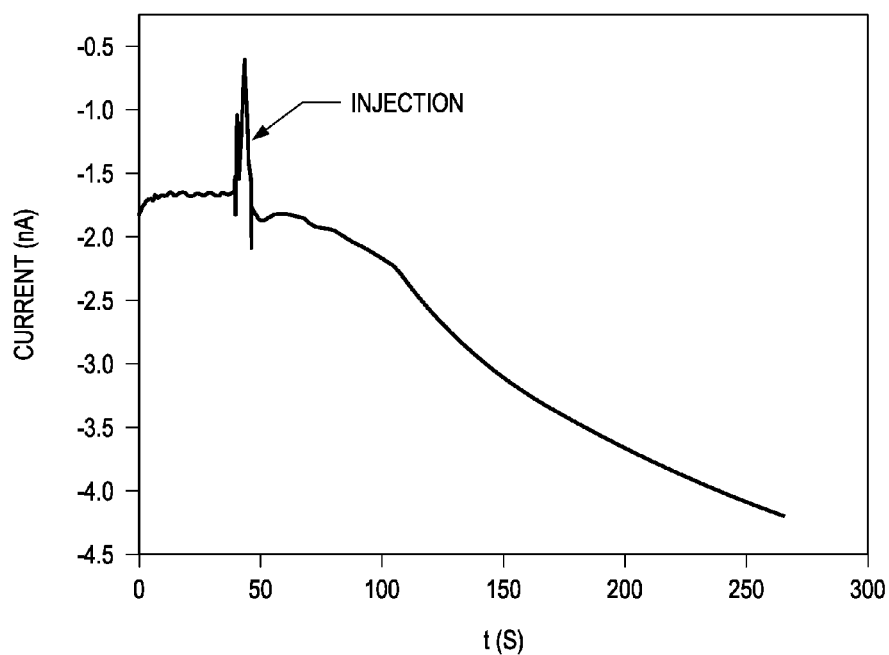
FIG. 2 is a graph of a current-time (i-t) curve recorded before and after injecting 50 pM Pt NPs into a 10 mM $NaBH_4$, 0.1 M NaOH solution, potential, −0.7V.

FIG. 2 is a graph of the i-t curve recorded before and after injecting 50 pM Pt NPs into a 10 mM NaBH$_4$, 0.1 M NaOH solution. The Pt particle concentration was about 50 pM and the electrode potential was −0.7 V vs Ag/AgCl. This inability to observe individual NP collisions has also been seen previously with other electrocatalytic systems (e.g., with Pt NPs stabilized with polyvinylpyrrolidone (PVP) on an Au electrode for hydrazine oxidation).

However, when the potential is scanned to more positive values, the current due to NaBH$_4$ oxidation at both Au and Pt UME decreases and drops to near zero at potentials>0.5 V (vs Ag/AgCl). This is caused by the gradual formation of adsorbed oxygen or oxide films on the metal electrodes. Oxidized Pt and Au are not electrocatalytic toward NaBH$_4$ oxidation, as with many other reactions that occur at the metal surface, e.g. hydrogen oxidation.

Figure 3A:
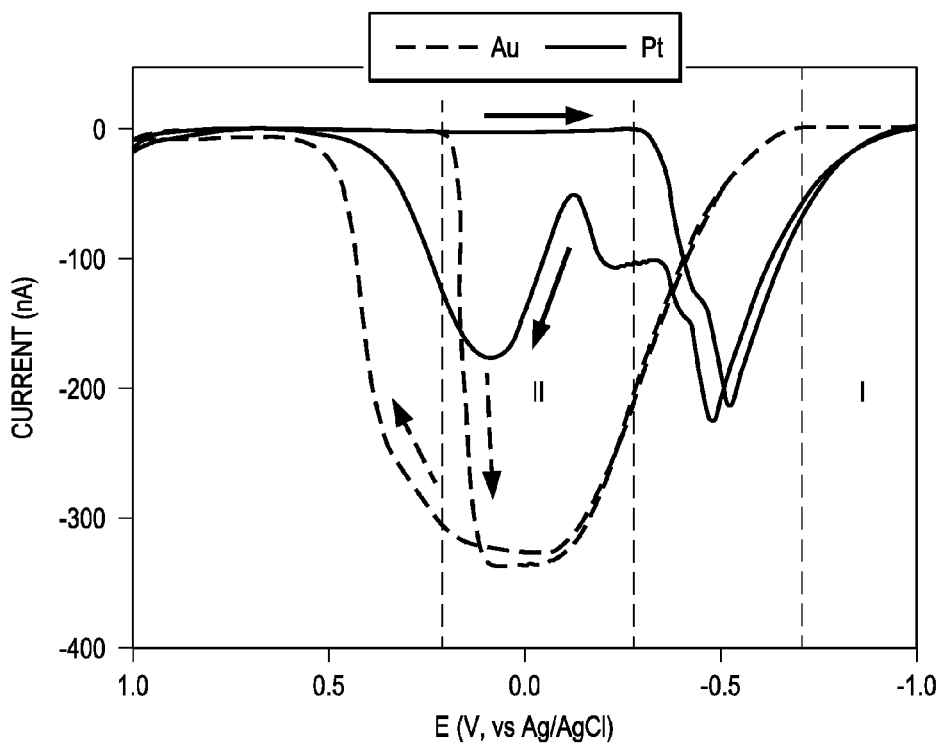
FIG. 3A is a cyclic voltammogram of Au and Pt UMEs in 10 mM $NaBH_4$, 0.1 M NaOH solution.
Figure 3B:
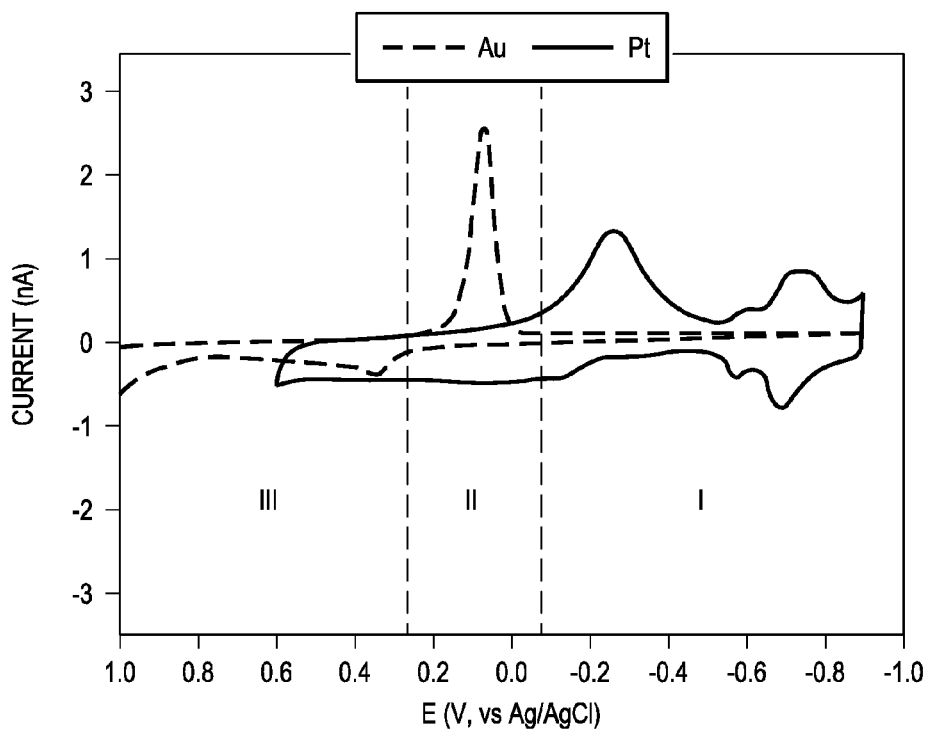
FIG. 3B is a cyclic voltammograms of Au and Pt UMEs in 0.1 M NaOH solution.

FIG. 3A are cyclic voltammograms of Au and Pt UMEs in 10 mM NaBH$_4$, 0.1 M NaOH solution. FIG. 3B are cyclic voltammograms of Au and Pt UMEs in 0.1 M NaOH solution. (Diameter of both UMEs, 10 μm; sweep rate, 100 mV/s). When the potential is scanned back in the negative direction, the oxidation current at a Au UME increases, starting at about 0.2 V (vs Ag/AgCl), but the oxidation current at a Pt UME remains near zero until about −0.25 V (vs Ag/AgCl) (region II in FIG. 3A), because Au oxide is easier to reduce than Pt oxide (FIG. 3B). Thus in region II, Au metal and Pt oxide are the stable forms. In this potential window we could observe collisions of single Au NPs on an oxidized Pt UME.

Two rapid sequential potential steps applied to grow a Pt oxide layer (first step) and then observe collisions (second step). These two steps must be applied with no delay between them, or else the Pt oxide will be reduced by the NaBH$_4$ at open circuit (i.e. the steady state open circuit potential (OCP) of the Pt UME is always about −1 V in NaBH$_4$ solution). By contrast, in the absence of NaBH$_4$ in 0.1 M NaOH solution the OCP shifts positively depending on the thickness of the oxide layer (e.g. from −0.90 V to 0.65 V after oxidation at 0.9 V for 10 s) and remains as a stable layer, e.g. at 0 V, until electrochemically or chemically reduced.

A Pt UME was first oxidized at 0.9 V (vs Ag/AgCl) for 10 seconds and then held at 0 V (vs Ag/AgCl) immediately followed by injection of the Au NPs, synthesized by the citrate reduction method. The average particle size was about 14±0.5 nm. TEM images and UV-vis spectra of these Au NPs are shown in FIG. 4.

Figure 4A:
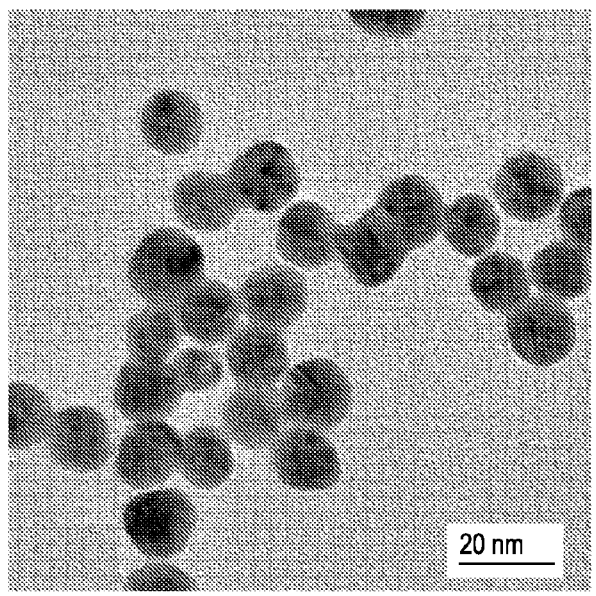
FIG. 4A is a TEM image and FIG. 4B is a UV-vis spectrum of citrate reduced Au NPs.
Figure 4B:
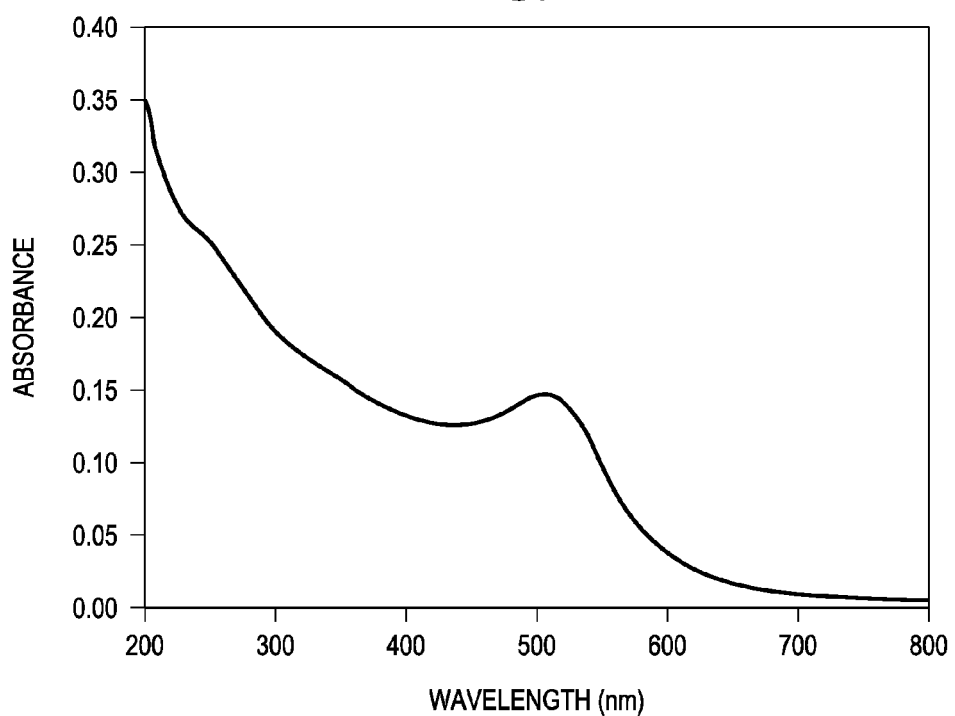

FIG. 4A is a TEM image and FIG. 4B is a UV-vis spectrum of citrate reduced Au NPs. The number of Au atoms, n, in a NP (about 84,700) was roughly calculated by the mass ratio of a NP and an atom as shown in the equation below.

$$n = \pi \rho d^3 N_A / 6M \tag{1}$$

Where ρ is the density of gold, d is the diameter of the Au NP, $N_A$ is the Avogadro constant and M is the molar mass of Au. The Au NP stock solution contained about 4.7 μM of particles. At the start of the measurement, an amount of Au NP stock solution that would produce a ~5 to 40 pM concentration was injected into the solution. The solution was then stirred by bubbling Ar gas for 5 to 10 seconds to disperse the NPs.

The current-time (i-t) response was recorded after lifting the Ar gas tube out of the solution.

Figure 5A:
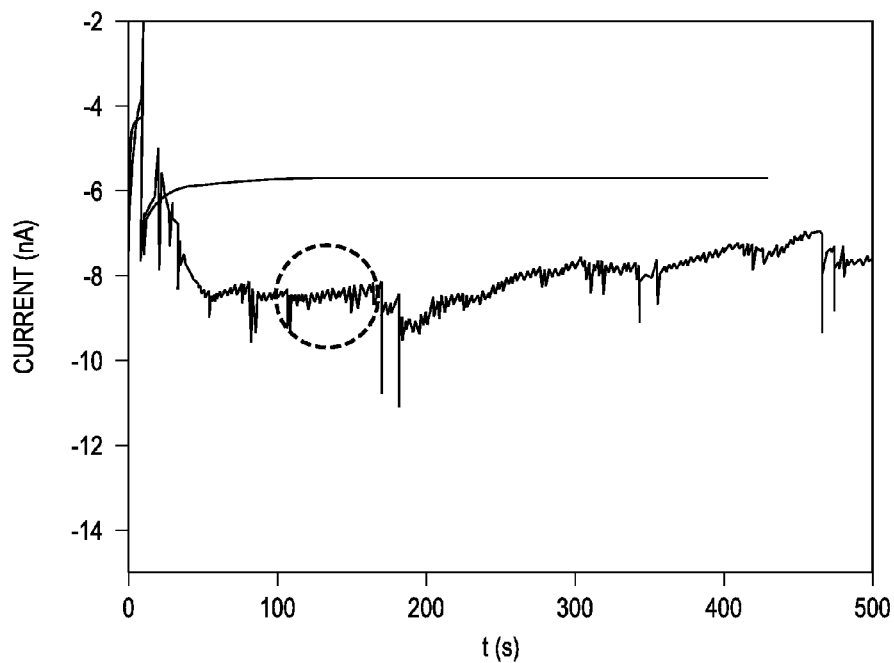
FIG. 5A is a current-time (i-t) curve without (upper curve) and with (bottom curve) injected Au NPs at pre-oxidized Pt UME. UME diameter, 10 μm; NP concentration, 24 pM, potential, 0 V.
Figure 5B:
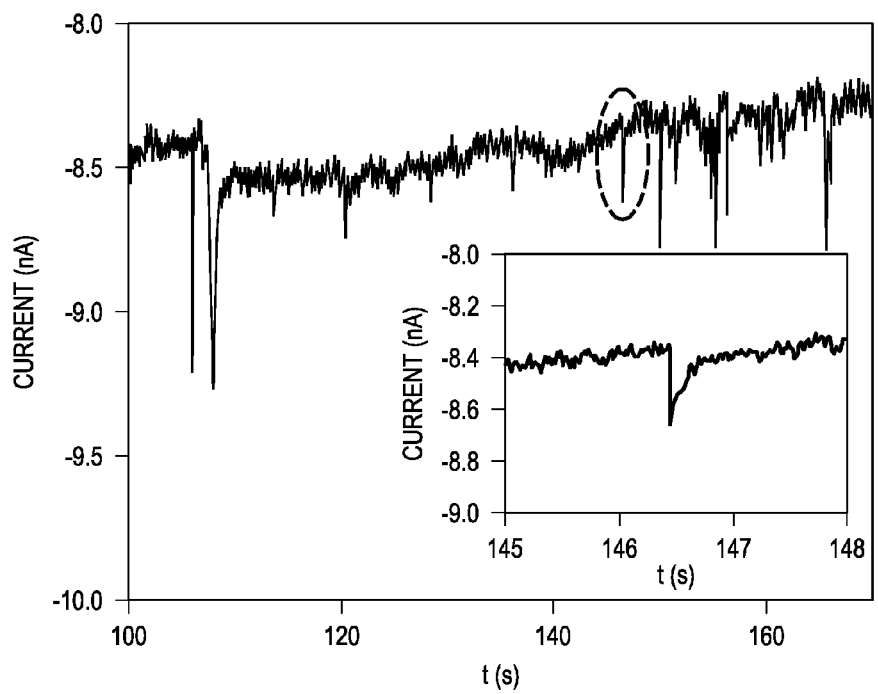
FIG. 5B is a zoom-in of the marked region on the panel of FIG. 5A.
Figure 5C:
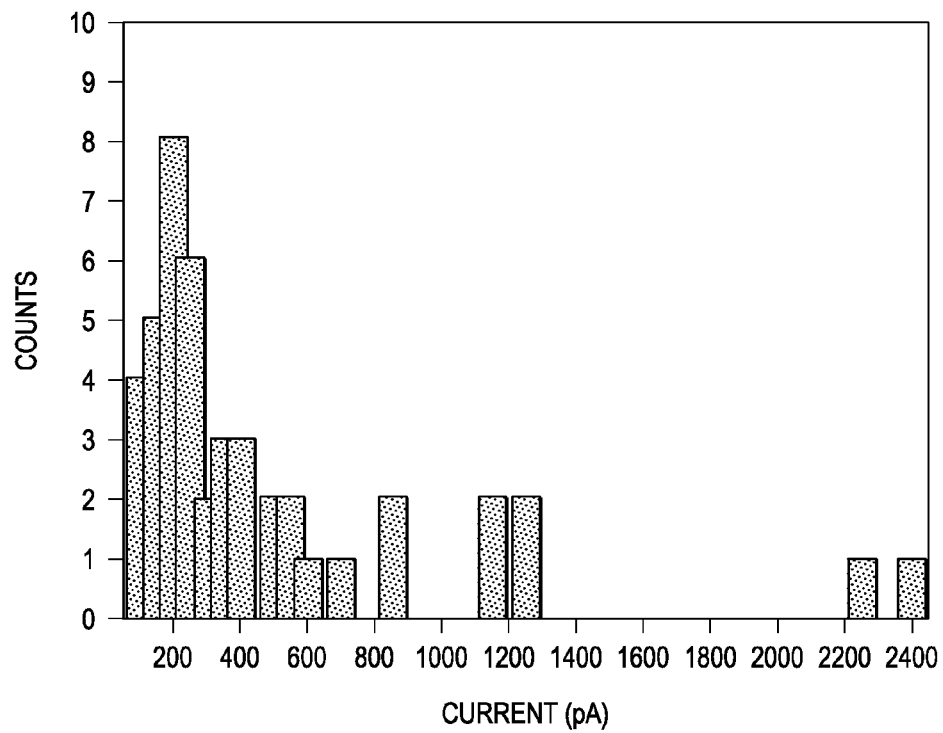
FIG. 5C is a statistical distribution of amplitudes of current peaks.

FIG. 5A is an i-t curve without (upper curve) and with (bottom curve) injected Au NPs at pre-oxidized Pt UME. UME diameter, 10 μm; NP concentration, 24 pM, potential, 0 V. FIG. 5B is a zoom-in of the marked region on panel of FIG. 5A. Inset is a single collision peak. FIG. 5C is a statistical distribution of amplitudes of current peaks. FIG. 5A is a typical i-t curve (after 10 seconds) on a pre-oxidized (first 10 seconds) Pt UME before and after injection of the citrate-reduced Au NP solution. After oxidation at 0.9 V, the thin oxide layer on Pt blocked most of the active sites for NaBH$_4$ oxidation resulting in a small background current. The surface oxidation state was estimated by calculating the ratio of reduction charge of PtO$_x$ ($Q_O$) and hydrogen adsorption charge ($Q_H$) in 0.1 M NaOH solution. After oxidation at 0.9 V for 10 seconds, the $Q_O/Q_H$ was about 3.3. The ratio of $Q_O/Q_H$ increases at more positive potentials, but remained constant when the electrode was at open circuit. The ratio decreased very slowly when the electrode was held at 0 V after oxidation at 0.9 V, indicating that the PtO$_x$ layer produced was stable in the NaBH$_4$ solution at 0 V (note that 0 V is still positive of the reduction peak of PtO$_x$).

Once Au NPs contacted the Pt/PtO$_x$ electrode, the oxidation of NaBH$_4$ could occur on active sites of the Au NPs, via electrons transferred by tunneling through this thin oxide film, providing the needed electrocatalytic amplification. Note that the Au NPs must be in contact with the electrode long enough so that the current observed is distinguishable from the background. However, the transient lasted only about 1 second and the current then returned essentially to background level (FIGS. 5A-5C). The individual current-time profile was affected by particle size, the particle residence time, and the nature of the interaction between the particle and the electrode surface. If NPs stick to the electrode surface after collision, a steady-state current would be achieved on each NP and the oxidation current would increase in a staircase response as observed previously on Pt NP collisions. Here the current profiles are more peak-like rather than steps, indicating the NPs leave or are deactivated after collisions. Depending on the residence times of Au NPs on the electrode, different amount of charge would be transferred; this determines the amplitudes of the peaks shown in FIGS. 5A-5C. Most of the peaks were in the range of 100 to 400 pA, which are smaller than the estimated steady state diffusion-controlled current for a 14 nm Au NP to oxidize 10 mM NaBH$_4$, about 1 nA. Several larger peaks>1 nA were seen, but these are probably collisions of aggregates of NPs. The charge transferred in a typical collision is around $4 \times 10^{-11}$ C for a current peak of 300 pA as shown in FIG. 5B. This amount of charge is much higher than that to simply charge or oxidize the whole Au NP (around 1.4 to $4 \times 10^{-14}$ C, assuming n=1 to 3 per Au atom). Thus, these peaks originate from catalyzed NaBH$_4$ oxidation rather than the Au NP itself, which would not be distinguishable from the background.

These peaks are associated with collisions of Au NPs on the Pt/PtO$_x$ UME. (1) The concentration of Au NPs in the solution was varied and the frequency of the collision was found to be essentially proportional to the particle concentration.

Figure 6A:
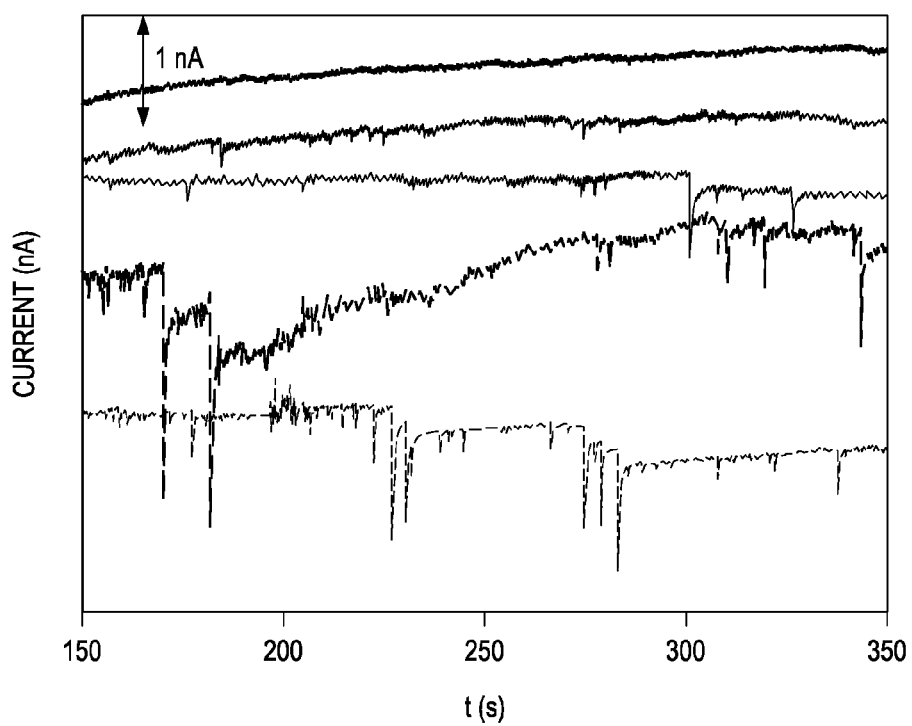
FIG. 6A is a current-time (i-t) curve recorded on a pre-oxidized Pt UME (10 μm) at 0 V in the presence of different concentrations of Au NPs, from top to bottom, 0, 6, 12, 24, 36 pM; electrolyte, 10 mM NaBH$_4$, 0.1 M NaOH.

FIG. 6A is a current-time curve recorded on a pre-oxidized Pt UME (10 μm) at 0 V in the presence of different concentrations of Au NPs, from top to bottom, 0, 6, 12, 24, 36 pM; electrolyte, 10 mM NaBH$_4$, 0.1 M NaOH.

Figure 6B:
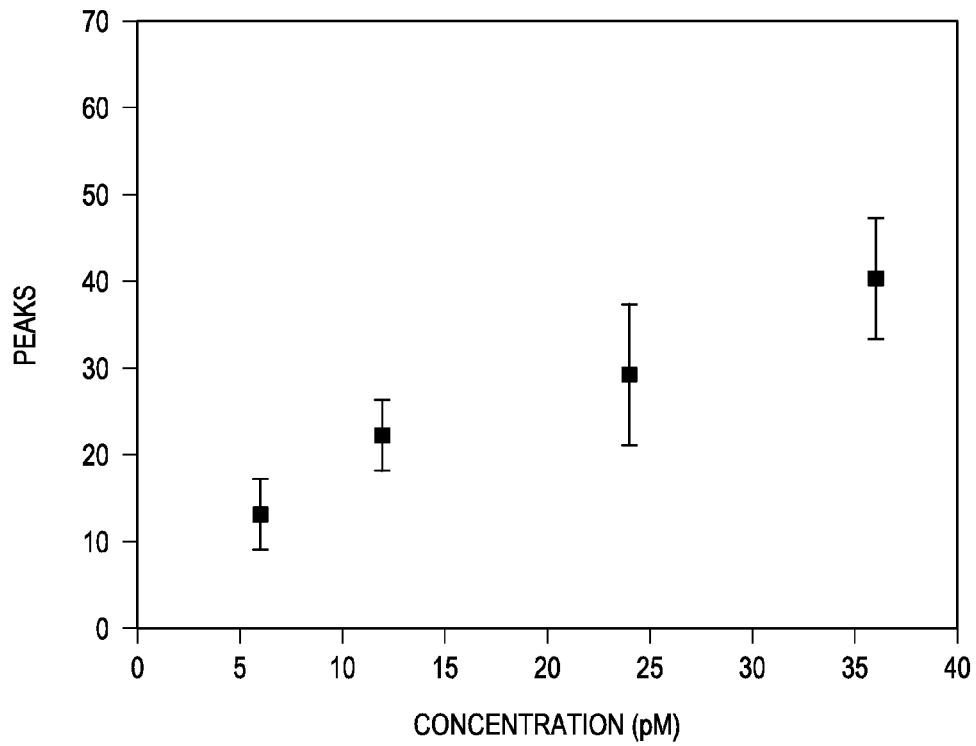
FIG. 6B is a graph of peaks counted in the time interval of 200 s under different concentrations.

FIG. 6B is a graph of peaks counted in the time interval of 200 s under different concentrations. The frequency is roughly 0.01 s$^{-1}$pM$^{-1}$; (2) After the UME was oxidized at 0.9 V, 50 pM Pt NPs (NaBH$_4$ reduced, citrate stabilized) were first injected and followed by injection of 20 pM Au NPs. No peaks appeared before injection of Au NPs (FIG. 7).

Figure 7:
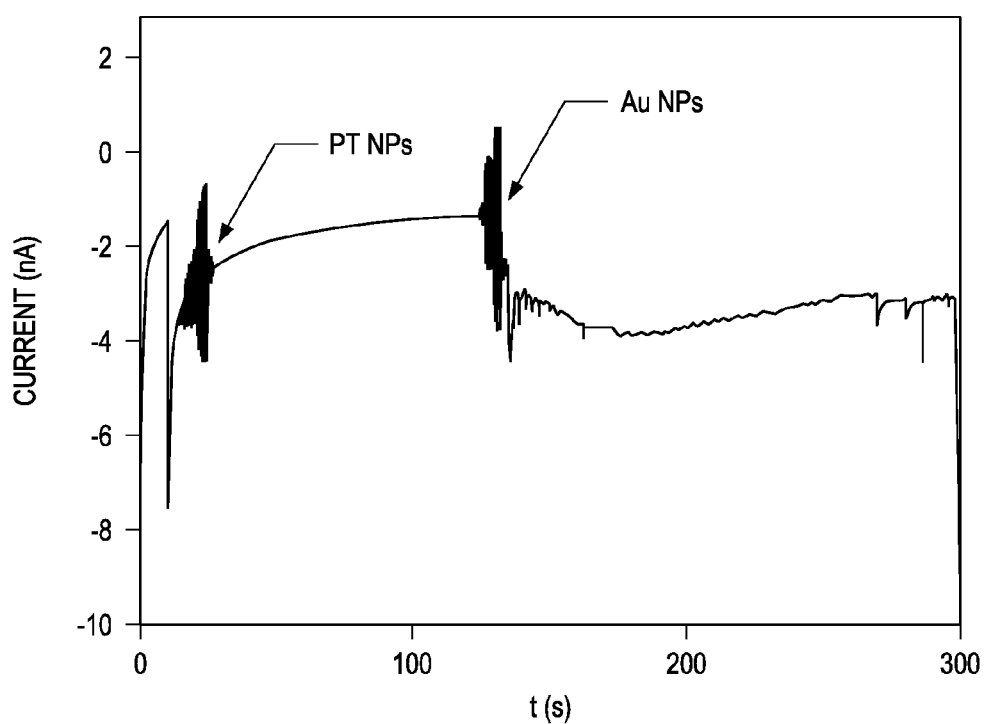
FIG. 7 is a current-time curve recorded on a pre-oxidized Pt UME (10 μm) at 0 V after injection of 50 pM Pt NPs and 20 pM Au NPs separately. Electrolyte, 10 mM NaBH$_4$, 0.1 M NaOH.

FIG. 7 is a i-t curve recorded on a pre-oxidized Pt UME (10 μm) at 0 V after injection of 50 pM Pt NPs and 20 pM Au NPs separately. Electrolyte, 10 mM NaBH4, 0.1 M NaOH. (3) The bias potential of a Au UME was varied from 0 V to 0.6 V. The oxidation current strongly depended on the potential, which determines the extent of oxidation of Au surface.

Figure 8:
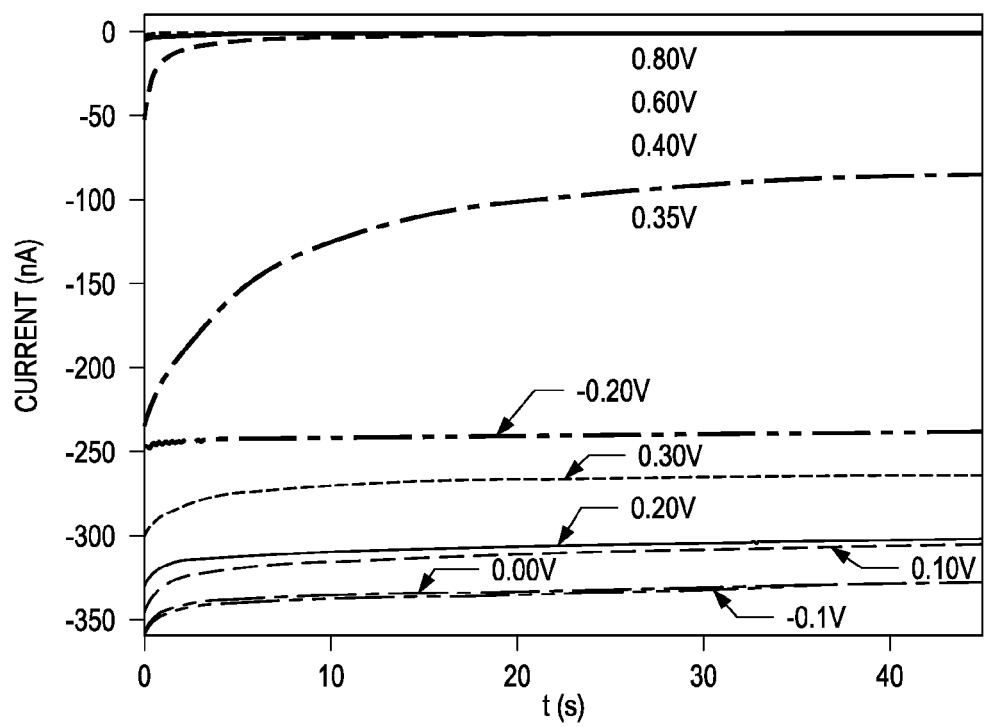
FIG. 8 is a current-time (i-t) curve recorded on a Au UME (10 μm) in 10 mM NaBH$_4$, 0.1 M NaOH at different potentials.

FIG. 8 is a i-t curve recorded on a Au UME (10 μm) in 10 mM NaBH$_4$, 0.1 M NaOH at different potentials. FIG. 8 is a plot of the effect of potential on current (current taken at 10 seconds from each potential step result in FIG. 8. At potentials>0.4 V, the surface of Au is oxidized and loses electrocatalytic activity for borohydride oxidation. The oxidation currents dropped to almost zero. The collision peaks observed at different potentials agree well with this finding.

Figure 9:
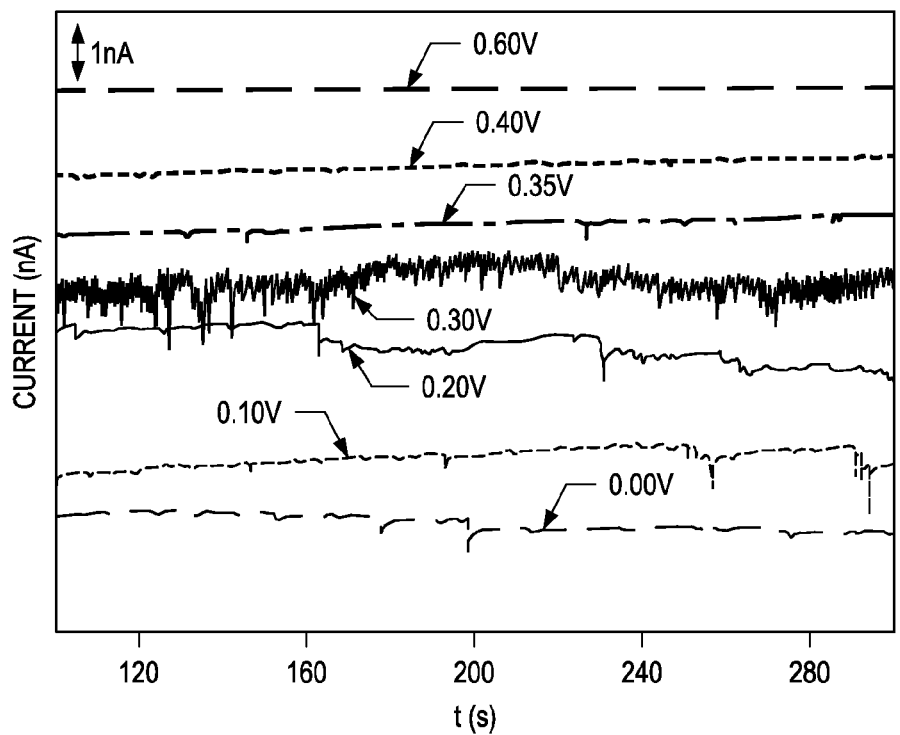
FIG. 9 is a graph of the effect of holding potential on collision peaks.

FIG. 9 is a graph of the effect of holding potential on collision peaks. FIG. 9 shows i-t curves recorded on a pre-oxidized Pt UME (10 μm) held at different potentials in the presence of 12 pM Au NPs. Electrolyte, 10 mM NaBH$_4$, 0.1 M NaOH. With increasing potential, the peak heights decreased and above 0.4 V, very few or no peaks were found.

The collisions of single Au NPs on a modified electrode have been demonstrated. This approach combines the advantage of using Pt UMEs and Au NPs. This greatly facilitates further investigations of the effects of particle size, shape and stabilizing agent on the collision behavior. Moreover, Au NPs are of interest as labels because of their bio-compatibility, tunable optical properties and good control of size and shape. Preliminary experiments have been carried out using this strategy with other electrodes. For example, a thin film of Ni deposited on a Pt UME forms an oxide film and blocks NaBH$_4$ oxidation in 0.1 M NaOH, but allows collisions of Pt NPs at 0 V (without previous oxidation) to be observed. Other strategies for surface and NP modification and alternative electrocatalytic reactions are currently under investigation.

The Pt UME was prepared following the general procedure developed in our laboratory. Briefly, a 10 μm platinum wire was sealed in glass after rinsing with ethanol and water. The electrode was then polished with alumina powder water suspension to a mirror face. The surface area was checked with standard redox electrochemistry of ferrocenemethanol. All the electrochemical experiments were performed using a CHI model 660 potentiostat, with the three-electrode cell placed in a Faraday cage. A 0.5 mm diameter tantalum wire was used as counter electrode, and the reference electrode was Ag/AgCl in saturated KCl solution (the reference electrode was further protected from the solution by a KNO$_3$ salt bridge). All potentials are quoted vs Ag/AgCl. We selected no filters for potential, current, and current converter in the CHI software. The sampling time was 10 ms.

The gold NP solution was prepared by first boiling 35 mL of a 0.4 mM aqueous HAuCl$_4$ solution. A 1.3 mL aliquot of 1% sodium citrate solution was injected under stirring. The solution was kept boiling for another 15 to 30 min. The solution obtained thereafter appeared ruby in color.

Before every experiment, the 0.1 M NaOH solution was deaerated with Ar and the Pt UME was subjected to a few potential cycles between 1 and −1 V. A multi-potential steps technique was applied and the Pt UME was held at 0 V immediately after first being oxidized at 0.9 V for 10 s. After a stable background was obtained at 0 V, the desired amount of Au NP stock solution was injected and the solution was stirred by bubbling Ar for about 5 to 10 seconds to uniformly disperse the NPs in the solution. After stirring, the Ar gas tube was lifted far above the solution surface and the current-time curve was recorded.

Previously, we tried to demonstrate that collisions could be observed on a metal electrode which has a layer of semiconductor oxide film (e.g., Ni, as in previous report). We also tried a W electrode. A W UME was obtained by electrochemical etching from 250 μm W wire. However, when sealing in glass, a color change of W wire was observed, indicating formation of oxide layer. Like Ni electrode, we did not observe any collision on W electrode.

The difficulties in observing collision behavior on these electrodes are due to (1) complicated behavior of electrode (many possible oxides, hydroxides, hydrates); (2) the difficulty in controlling the oxide film thickness (conductivity getting too low when film is too thick); and (3) the difficulty in getting a UME electrode (e.g., W electrode forms thick oxide layer when heated).

To overcome these difficulties, the present invention electrodeposited a layer on a Pt UME. This layer could be any material as long as it is conductive and electro-catalytically inert toward redox couple. Since this layer is deposited on a Pt UME, the electrode surface is small and the signal/noise level should satisfy the requirements for collision observation. The thickness of this layer could be controlled by deposition time and potential.

We tried (1) a layer of less noble metals, e.g. Cu or Ag, whose thickness is not an issue as long as it exists as metal; (2) a layer of transition metals, e.g. Ni, or Fe, whose thickness should be controlled carefully since it is very easy to oxidize; (3) a layer of other materials, which is inert and conductive, e.g., conductive polymers or carbon; on a UME Pt or Au electrode.

Figure 10:
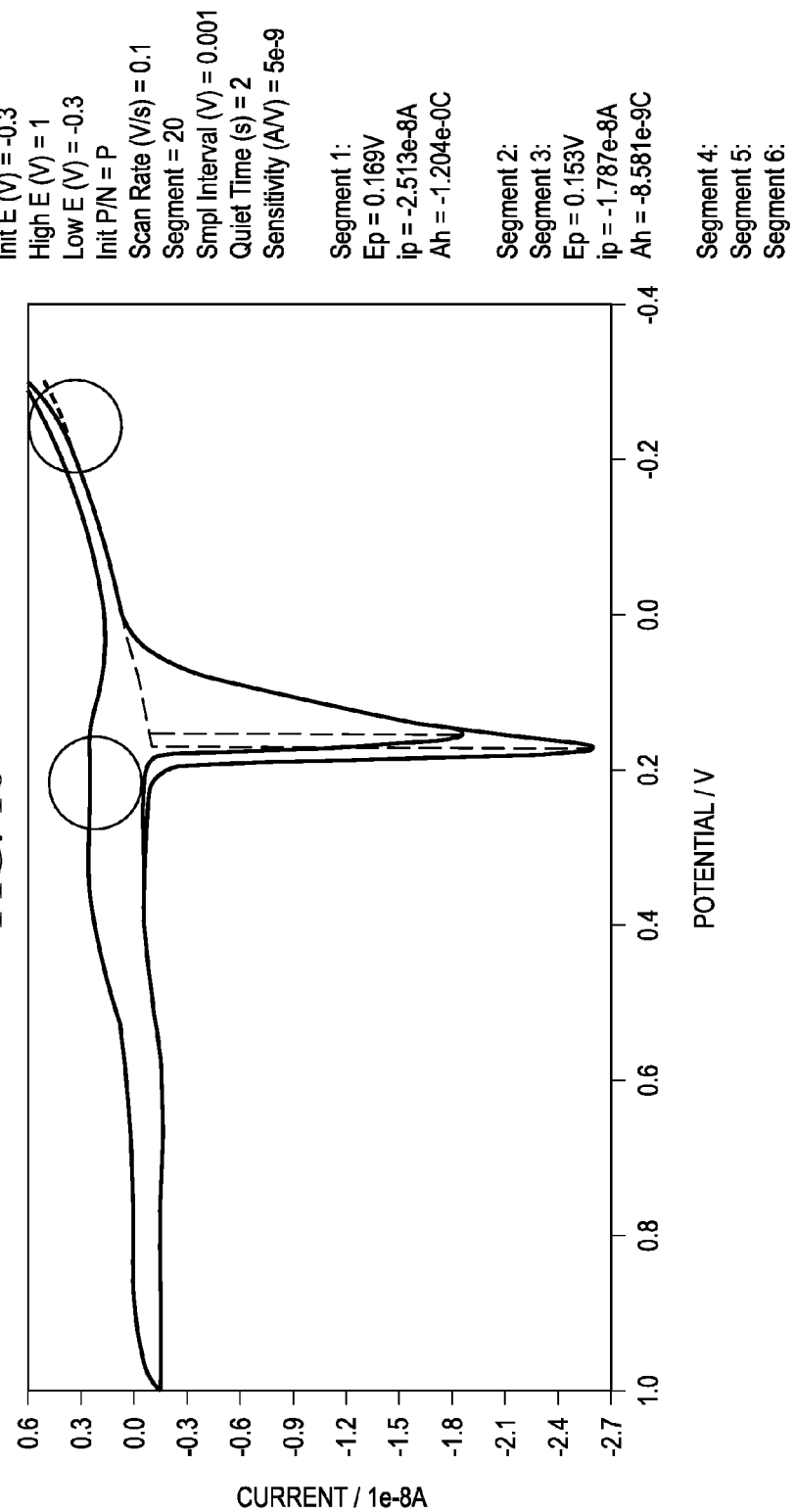
FIG. 10 is a cyclic voltammetry plot at a Pt UME (10 μm) in a solution of 1 mM CuSO$_4$ and 0.1 M H$_2$SO$_4$.
Figure 11:
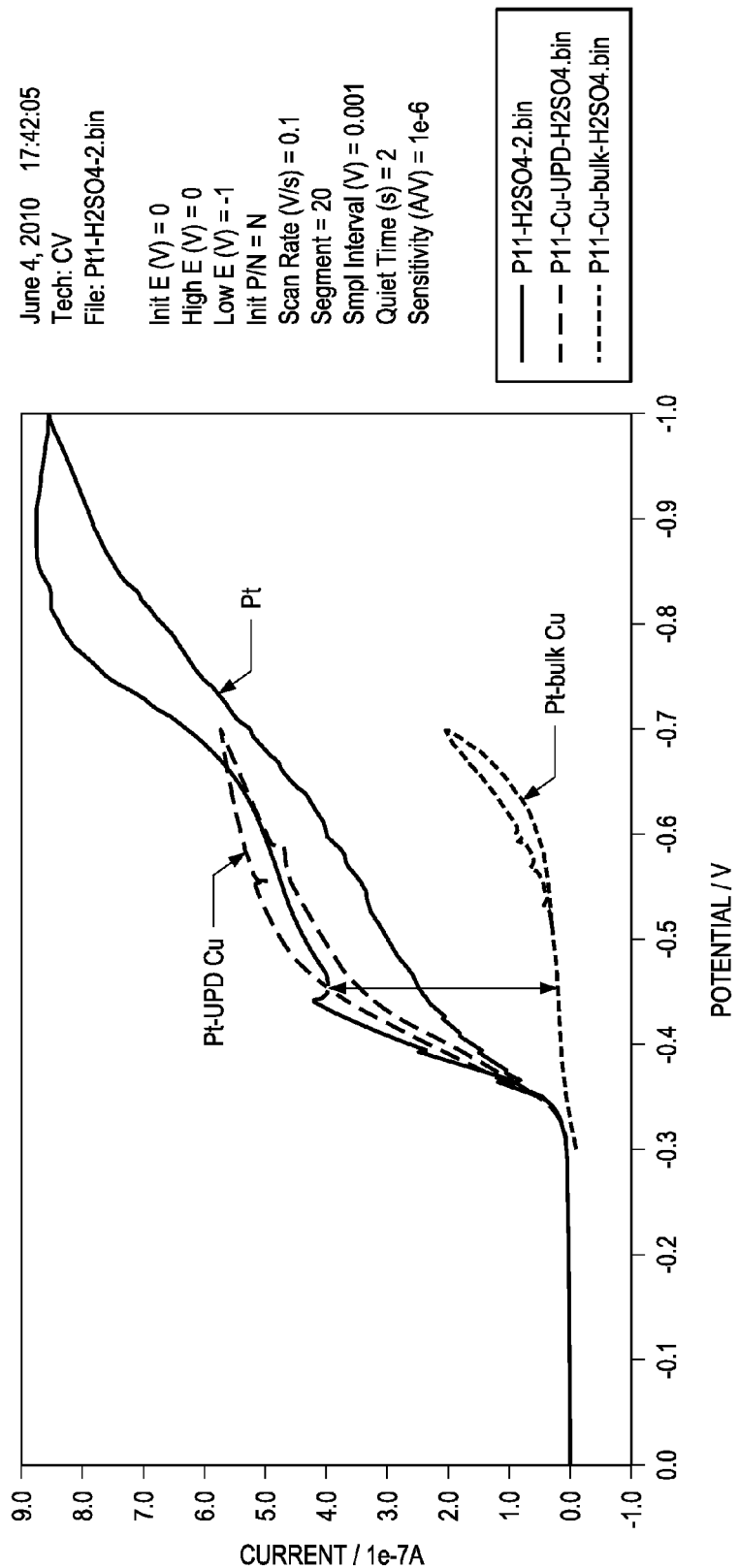
FIG. 11 is a cyclic voltammetry plot at different Pt UMEs with deposited Cu in a solution of 0.1 M H$_2$SO$_4$.

Electro-deposited Cu layer on Pt UME. FIG. 10 shows cyclic voltammetry at a Pt UME in a solution of 1 mM $CuSO_4$ and 0.1 M $H_2SO_4$. A small peak corresponding to copper under-potential deposition (UPD) starts around 0.4 V (vs. Ag/AgCl). The bulk deposition starts around 0 V. A comparison of electrode behavior after coating the copper layer under different potentials is shown in FIG. 11. Copper layer deposited at UPD (0.2 V) for 200 seconds does not block the Pt surface for hydrogen evolution. However, a copper layer deposited at –0.3 V for 200 seconds significantly blocks the Pt layer, which causes the negative shift of onset potential for hydrogen evolution. And this creates a potential window for possible collision observation. Since this potential window is essentially more negative than the onset potential for copper reduction, the layer will be metallic copper instead of copper oxide during collision experiment.

FIG. 11 is an image of a cyclic voltammetry at different Pt UMEs in a solution of 0.1 M $H_2SO_4$.

Figure 12:
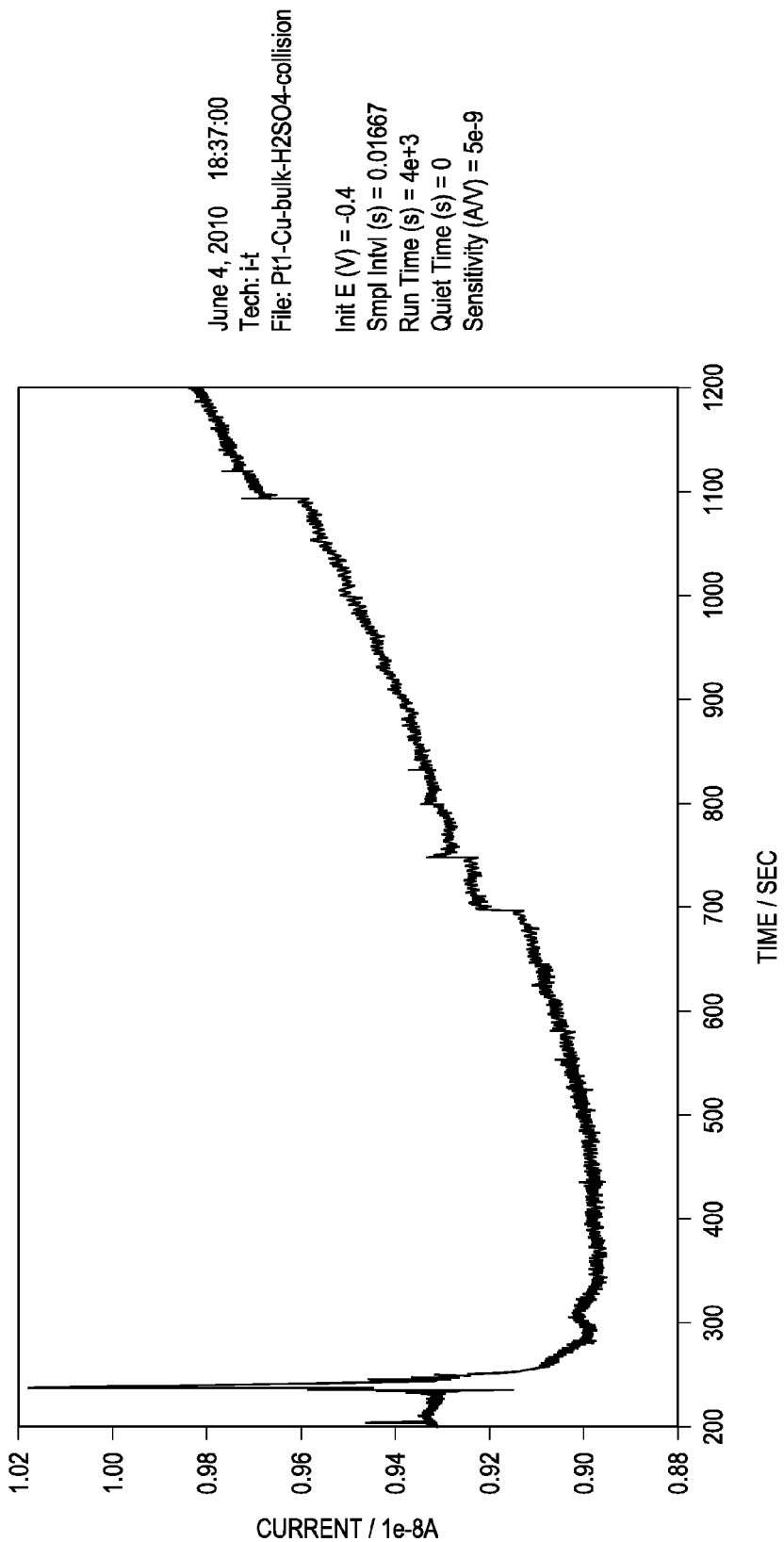
FIG. 12 shows a current-time (i-t) curve at a Pt—Cu UME after injection of 5 nM Pt NPs into a solution of 0.1 M H$_2$SO$_4$.

FIG. 12 shows an i-t curve at a Pt—Cu UME after injection of 5 nM Pt NPs into a solution of 0.1 M $H_2SO_4$. The current slowly but constantly increases and some big jumps could be seen.

Figure 13:
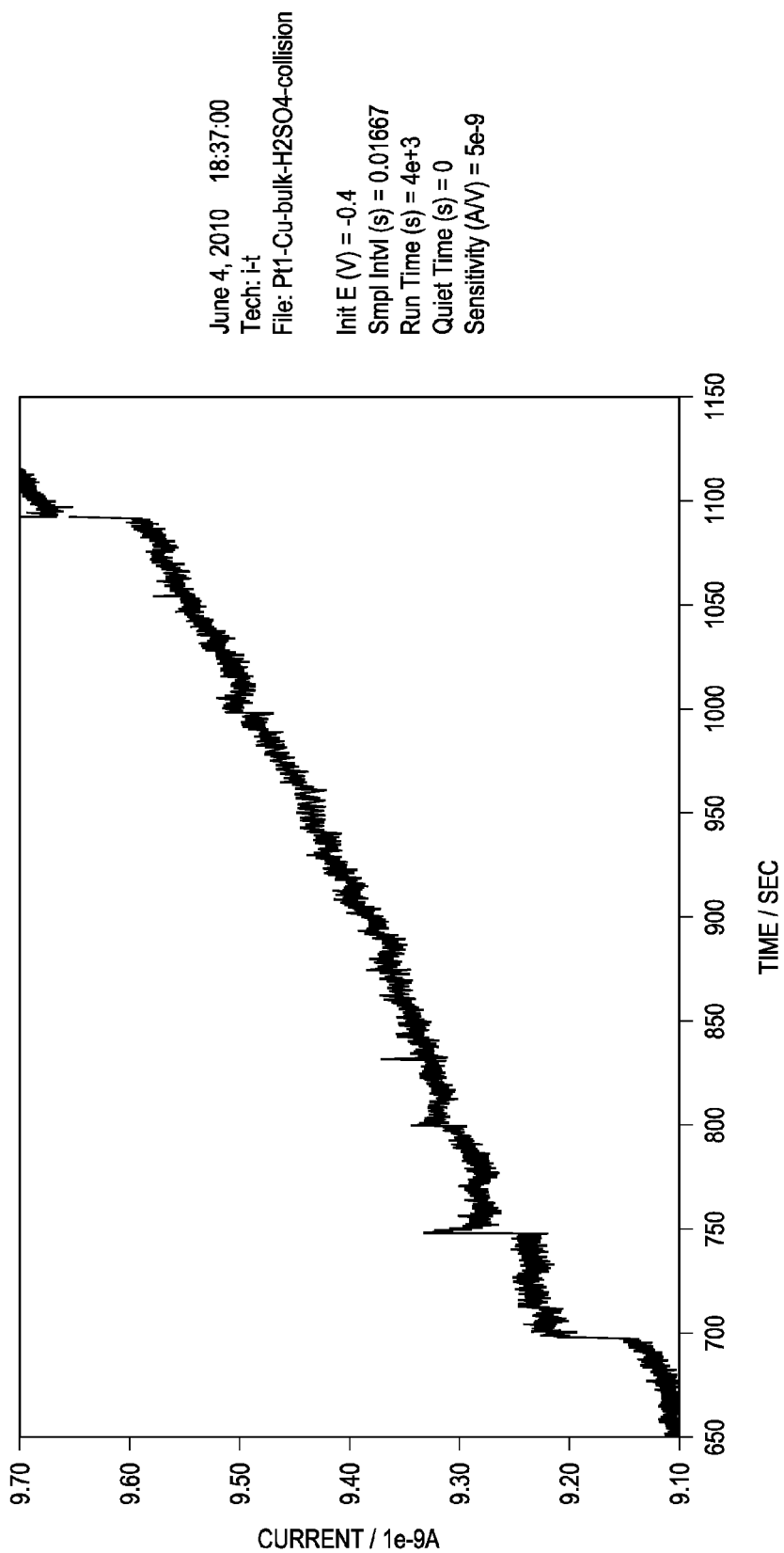
FIG. 13 is a zoom in from FIG. 12.

FIG. 13 is a zoom in from FIG. 12. The CV after collision was different from the one before collision (FIG. 14).

Figure 14:
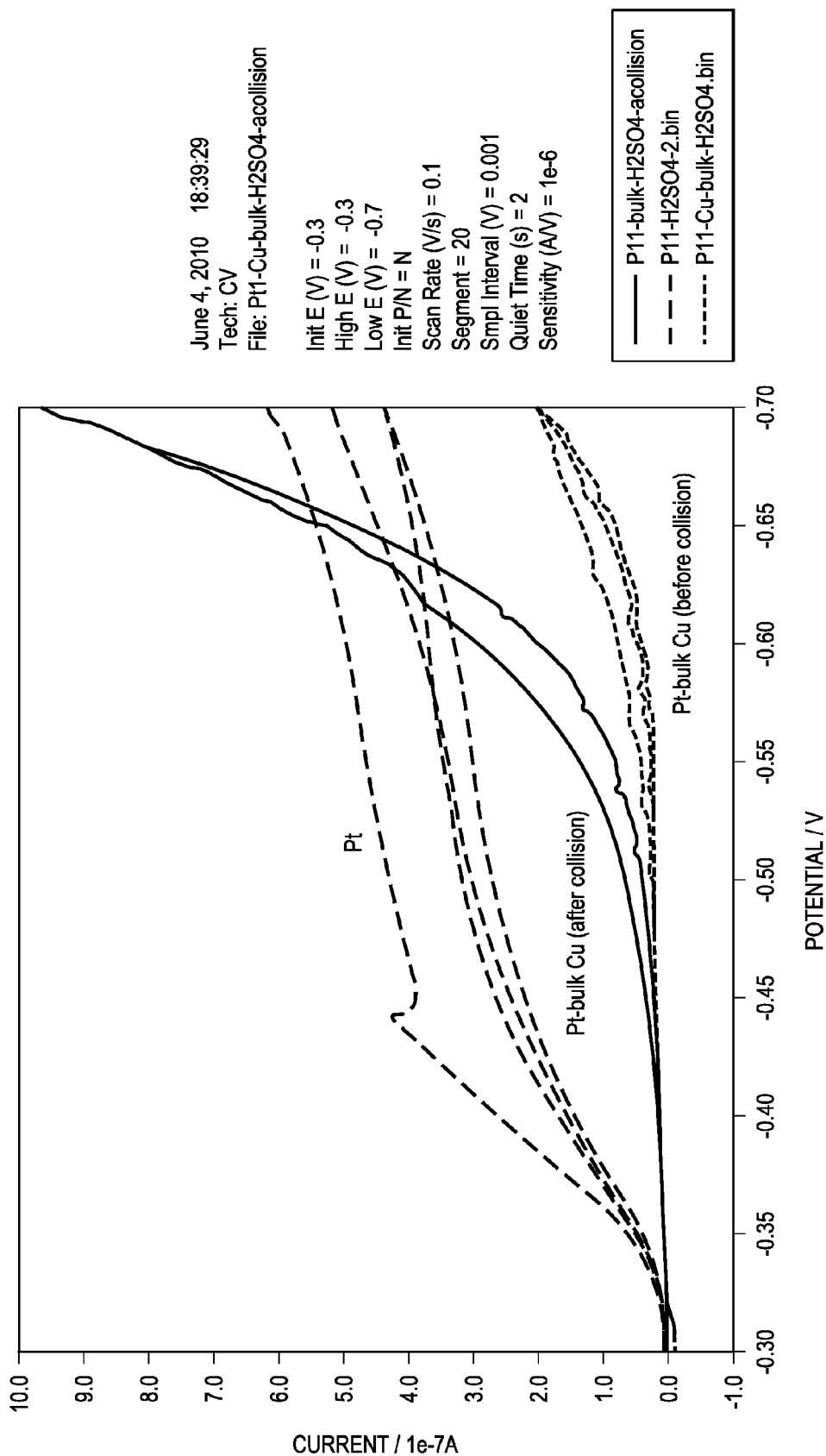
FIG. 14 is a cyclic voltammetry plot taken in 0.1 M H$_2$SO$_4$.

FIG. 14 is a plot of a cyclic voltammetry taken in 0.1 M $H_2SO_4$.

Figure 15:
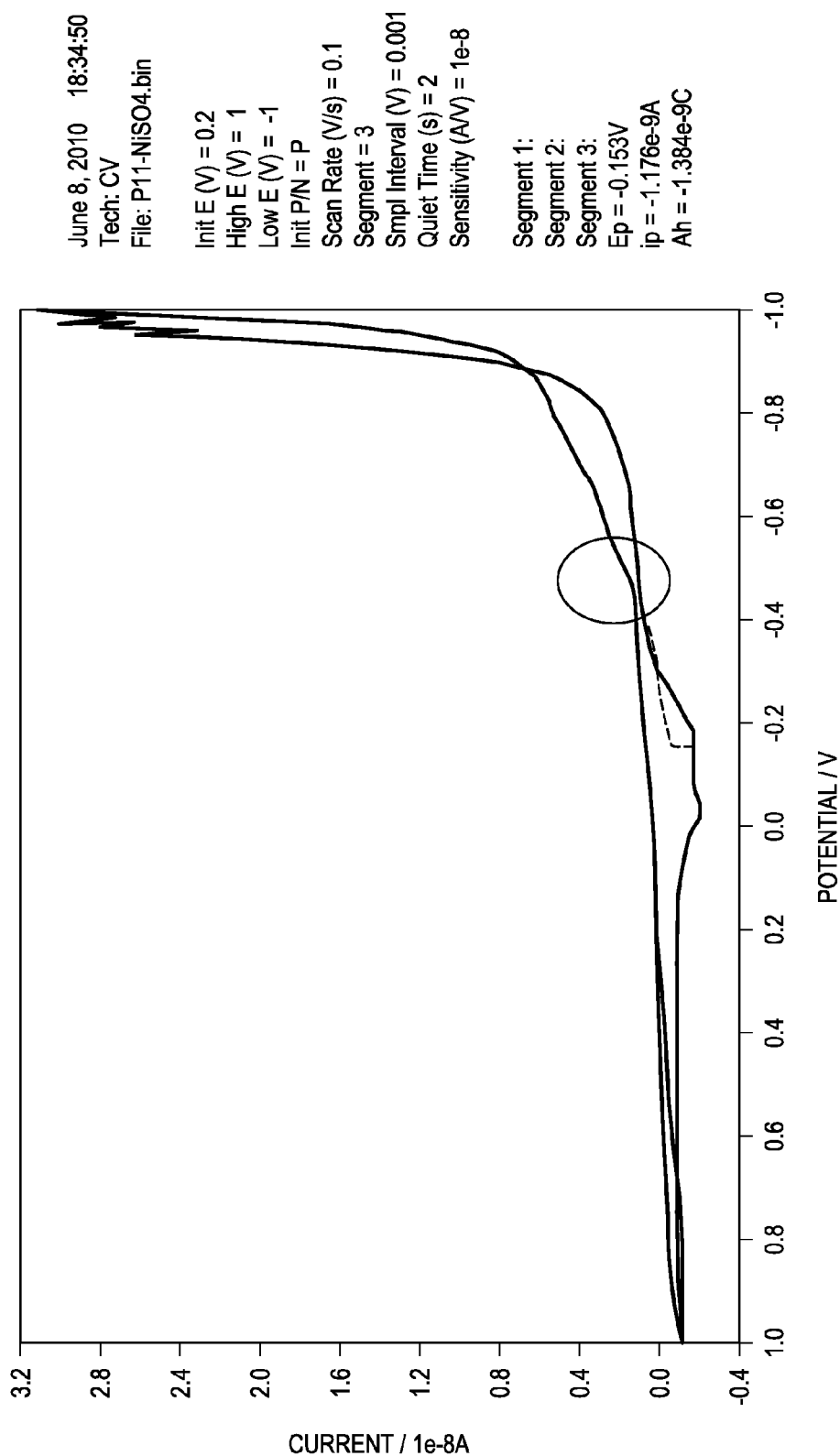
FIG. 15 is a cyclic voltammetry plot at Pt UME in 1M NiSO$_4$, 1.8 M boric acid, 0.15 M NaCl solution.
Figure 16:
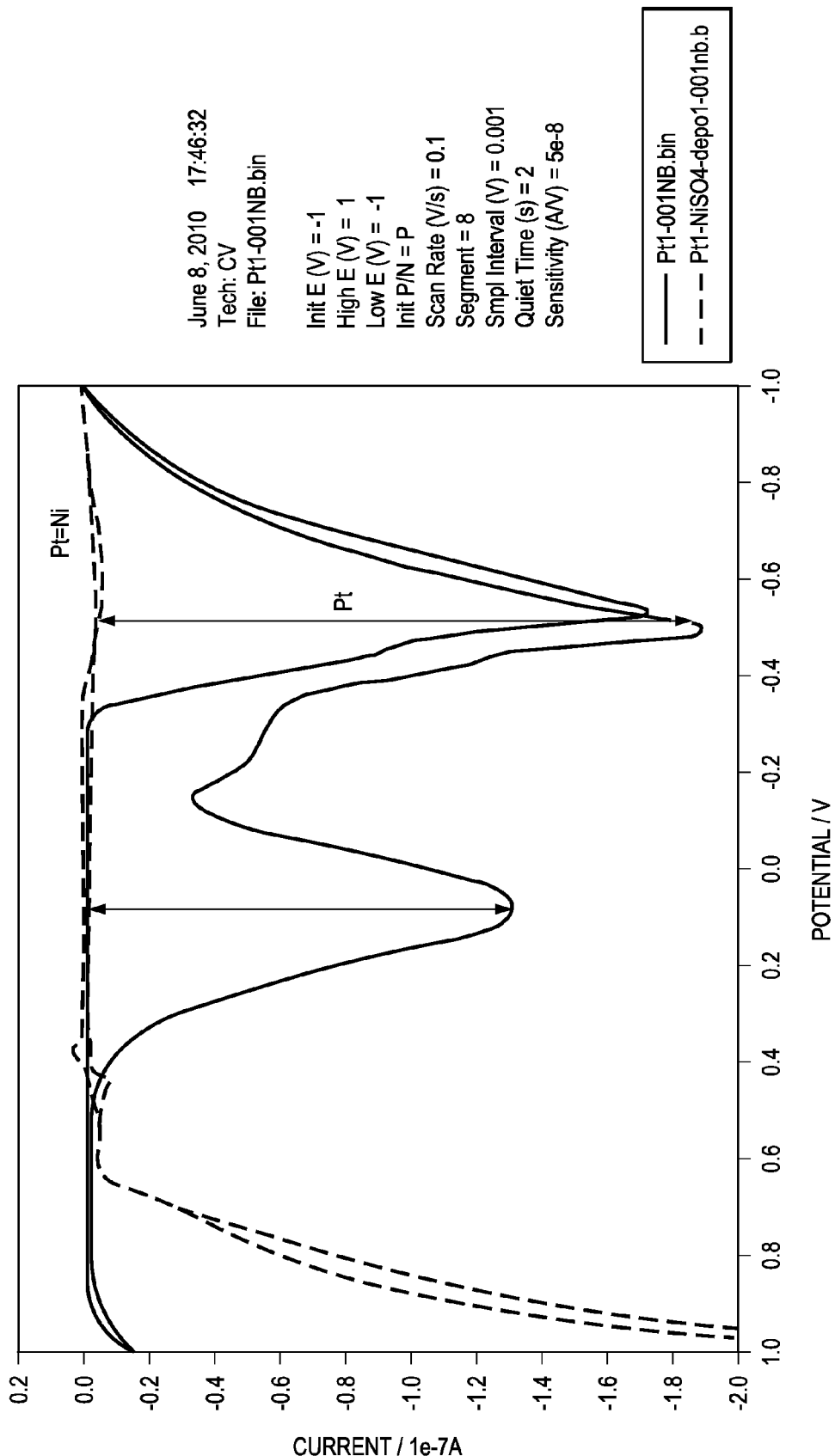
FIG. 16 is a cyclic voltammetry plot at Pt (red) and Pt—Ni (blue) in 0.1 M NaOH, 10 mM NaBH$_4$ solution.
Figure 17:
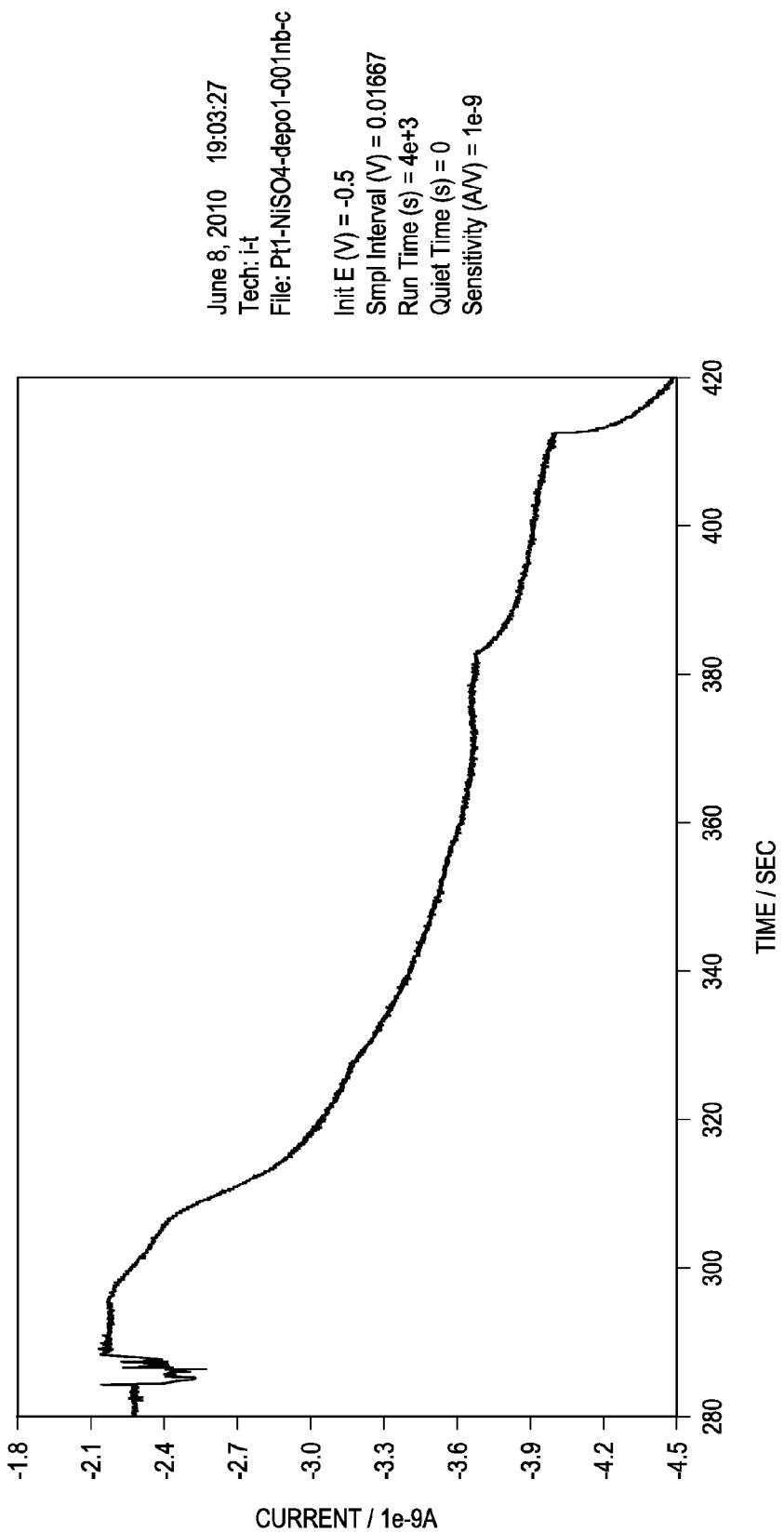
FIG. 17 shows a current-time (i-t) curve at Pt—Ni electrode in 0.1 M NaOH, 10 mM NaBH$_4$ solution.
Figure 18:
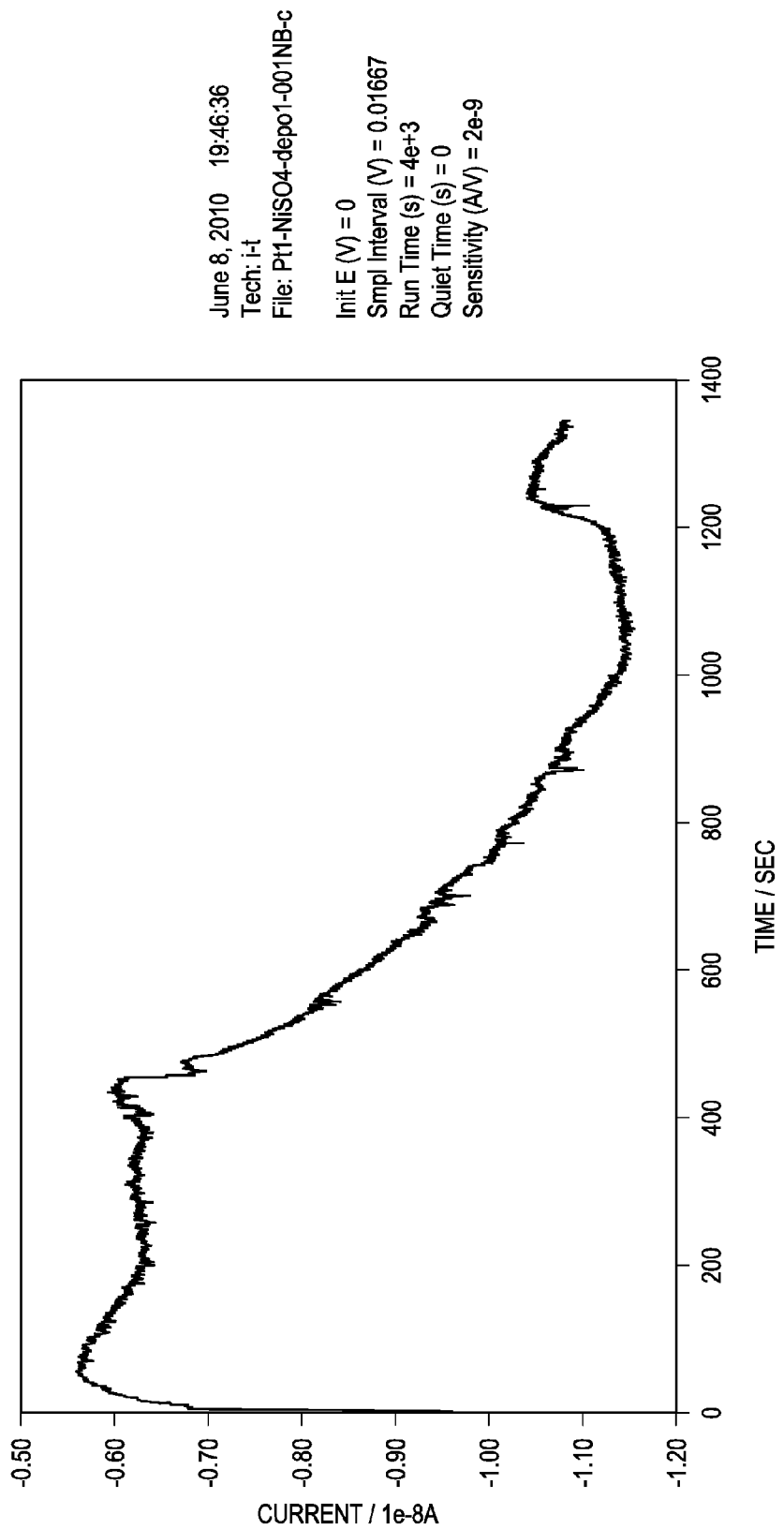
FIG. 18 shows a current-time (i-t) curve at Pt—Ni electrode in 0.1 M NaOH, 10 mM NaBH$_4$ solution.
Figure 19:
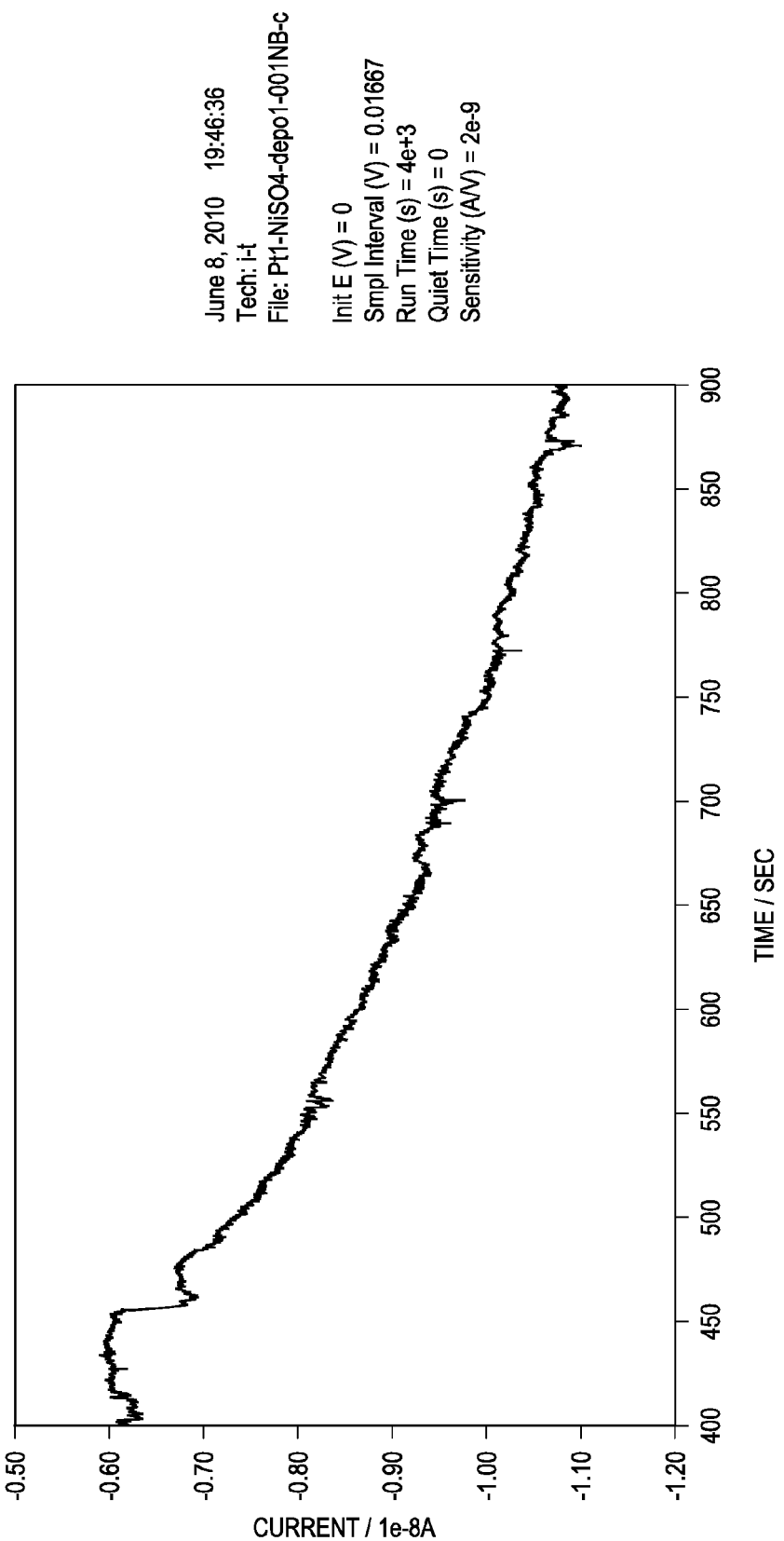
FIG. 19 is a zoom in from FIG. 18.

FIG. 15 shows cyclic voltammetry at Pt UME in 1M $NiSO_4$, 1.8 M boric acid, 0.15 M NaCl solution. Deposition of Ni was conducted in a solution of 1M $NiSO_4$, 1.8 M boric acid, 0.15 M NaCl at –0.5 V for 10 s (FIG. 15). The resulting Pt—Ni electrode was tested in 0.1M NaOH, 10 mM $NaBH_4$ solution. The behavior of Pt—Ni UME is different from Pt UME. As shown in FIG. 16, two potential windows are available for collision observation. At potential –0.5 V, after injection of Pt NPs (FIG. 17), the current constantly increases, which was also observed previously using Au NPs on Pt UME in this potential window. At potential 0 V, after injection of Pt NPs (FIGS. 18 and 19), steps corresponding to collisions were observed. At this potential, the Ni layer should be already oxidized. The electrode becomes Pt—$NiO_x$. Although the metallic Ni turns into oxide, the short deposition time (10 seconds) makes the layer thin and still conductive. The CV after collision is different from before.

Figure 20:
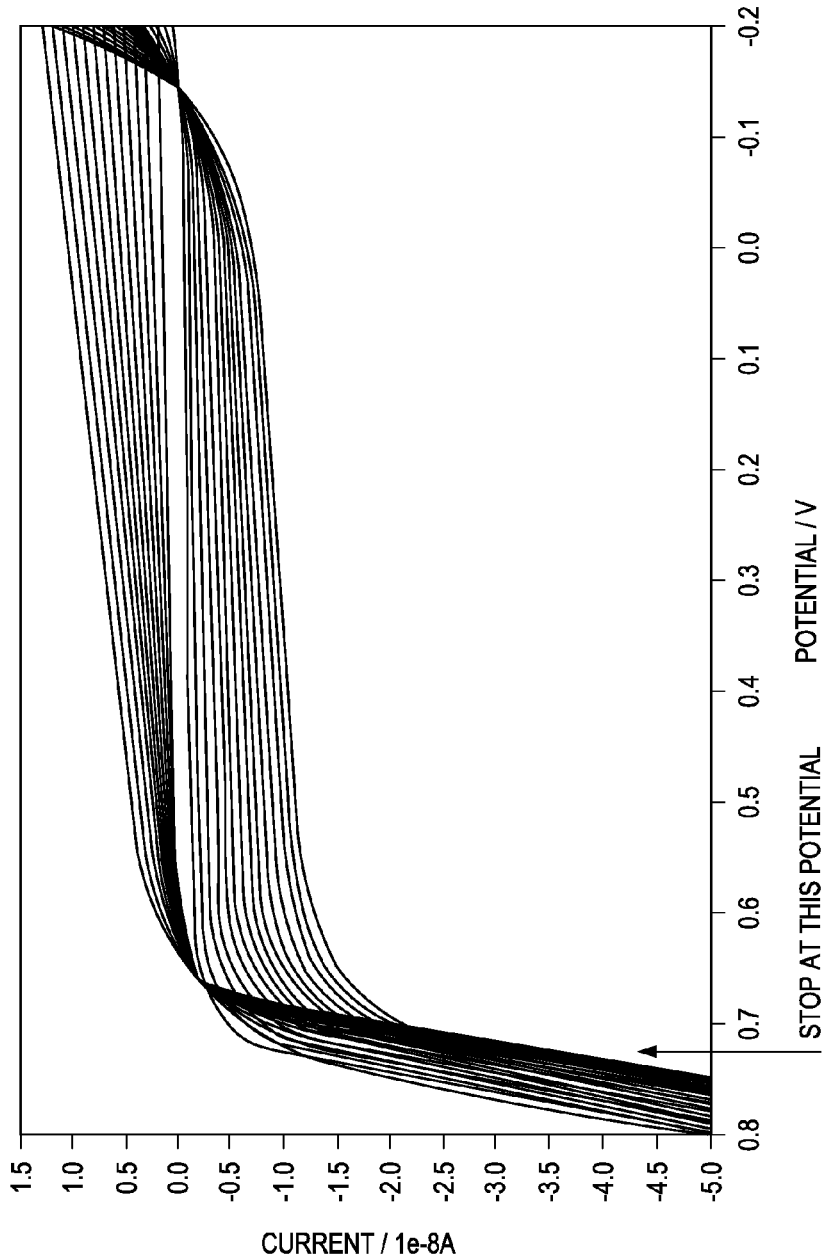
FIG. 20 is an electrodeposition plot of ppy film in 100 mM H$_2$SO$_4$, 30 mM pyrrole, 100 mM KNO$_3$ solution by potential cycles.

Electro-deposited conductive polymer (polypyrrole, ppy). The ppy layer was grown in a solution of 100 mM $H_2SO_4$, 30 mM pyrrole, 100 mM $KNO_3$ for 50-100 cycles and finished at ~0.7 V. The ppy film greatly reduces the oxidation current of hydrazine on Pt UME (FIG. 20). However, no collision signal was observed after injection of Pt NPs in hydrazine solution.

A detector or array of detectors can be used to detect nanoparticle collisions with the electrode, via signal amplification from the electrocatalytic ability of the nanoparticle for the redox reactant, e.g., the detector can count the number of collisions, the detector can measure nanoparticle collisions by monitoring current changes or the detector can classify the collisions into one or more types (e.g., the magnitude of the current increase can be used to classify the nanoparticle). In various embodiments, the detector can measure nanoparticle collisions by monitoring potential changes. For example, the electrode can be driven with a constant current. In the absence of nanoparticles, the electrode voltage required to pass the current can be large. Upon a nanoparticle collision, the required voltage can drop substantially; thus, fast, large voltage drops can be interpreted as a nanoparticle collision. The magnitude of the voltage drop can be used classify the nanoparticle, for example, by nanoparticle size. The time response can also be used to classify the nanoparticle, for example, into different residence times.

The present invention includes methods, compositions and kits for analyzing a chemical analyte having an electrochemical cell connected to a measuring apparatus. The electrochemical cell contains a solution having one or more metal nanoparticles, one or more chemical analytes, an indicator. In addition, the electrochemical cell contains one or more electrodes in communication with the solution. One or more electrocatalytic properties are generated by the interaction of the one or more metal nanoparticles and the liquid sample and measured at the one or more electrodes.

The present invention includes one or more nanoparticles in solution within the electrochemical cell. The nanoparticles may be entirely or partially metal or a carbonaceous or semiconductor material. For example, the one or more metal nanoparticles may be platinum nanoparticles, gold nanoparticles, silver nanoparticles, copper nanoparticles, ruthenium nanoparticles, palladium nanoparticles or mixtures and combinations thereof. The nanoparticles may also have cores of a different material than the outer material of the nanoparticle. Although, the nanoparticles may be of in diameter sized between about 0.5 nm and about 100 nm, a common size range for one embodiment is between about 1 nm and 7 nm in diameter and an average of 4 nm in diameter, or between about 12 nm and 16 nm in diameter and an average of 14 nm in diameter for Au NPs. Furthermore, the size distribution of nanoparticle diameter may be generally uniform, disperse, or varying. The nanoparticles may have different groups of particles that have generally the same diameter within the group but differing diameter relative to other groups in solution.

The electrochemical reactions can be driven by controlling the electrical potential of the electrode. The electrical potential of the electrode can be selected so that oxidation or reduction can occur at the electrode. The potential can be set to minimize currents resulting from the redox reactant in the absence of nanoparticles and from other electrochemical reactions. The potential can be set with respect to a counter electrode or with respect to a reference electrode. See Bard (2001) for details on these standard electrochemical techniques. For example, the electrical potential can be within 1 V of zero, with respect to the standard hydrogen electrode (SHE). For example, the electrical potential can be within 1 V of zero, with respect to the counter electrode. Smaller voltage magnitudes (e.g., 0.5 V, 0.3 V, 0.25 V, or 0.1 V) may also be useful. The electrical potential may vary in time or be constant. In certain embodiments, a constant potential can be used to eliminate capacitive transients due to double-layer charging of the electrode. In some embodiments, a current can be driven through the electrode, and the potential can be monitored. Upon contact of a nanoparticle, the impedance and the voltage are greatly reduced. Other schemes for driving the electrochemical reactions needed to monitor the presence of nanoparticles will be evident to those skilled in the art.

Upon contact of the nanoparticle on the electrode, the reaction rate for the redox reactant greatly increases. For example, the rate of reaction of the redox reactant attributable to the nanoparticle normalized to the nanoparticle's surface area can be at least 200 times greater than the rate of reaction of the redox reactant attributable to the electrode normalized to the electrode's surface area. If measuring current, the above statement can be mathematically expressed as $(i_{NP}-i_e)/A_{NP} > 200\ i_e/A_e$, where $i_{NP}$ is the current measured in the presence of a nanoparticle, $i_e$ is the current measured in the absence of a nanoparticle, and $A_{NP}$ and $A_e$ are the surface areas of the nanoparticle and electrode, respectively.

In various embodiments, the time response of electrode current can be measured. The current transient includes particle charging and a changing faradaic current for the electrocatalysis of redox reactant that attains steady state in a time $\sim r_{NP}^2/D_{RR}$. Since different types of collisions can occur, the current-time (i-t) transient for each collision event will be determined by the residence time of the nanoparticle at the electrode, i.e., the time period when the electrode can pass electrons to the nanoparticle. If the nanoparticle sticks to the electrode for a time sufficient for a steady state current to be attained, and the redox reactant is only converted to product at the particle, the amplification factor of the electrochemical current to charging current is given by the relative steady-state fluxes of the particles and RR is $\sim (B/16)(D_{RR}\ C_{RR}\ a)/(D_{NP}\ C_{NP}\ r_{NP})$.

Exemplary coating or capping compounds for stabilizing nanoparticles include alkanethiols, mercapto alcohols, mercaptocarboxylic acids, thiophenols, thiol-functionalized oligonucleotides, benzenedimethanethiol, oxalate, and citrate. Such stability-improving compounds are sufficiently small so that electron tunneling can still occur to enable charge transfer from the electrode to the nanoparticle It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of analyzing a sample using nanoparticle collision amplification at a surface modified electrode comprising the steps of:
   providing a sample chamber having at least 2 electrodes, wherein
   one or more of the at least 2 electrodes comprise a thin oxide film on the surface, wherein the thin oxide film has a thickness that inhibits an inner sphere reaction of the at least 2 electrodes and allows collisions of one or more nanoparticles;
   combining one or more metal nanoparticles with a liquid sample comprising at least one reactant within the sample chamber;
   wherein the at least one reactant comprises sodium borohydride ($NaBH_4$) as a heterogeneous inner sphere reductant;
   contacting the one or more metal nanoparticles with the thin oxide film and the at least one reactant;
   generating one or more electrocatalytic properties at the thin oxide film by the oxidation or reduction reaction between the one or more nanoparticles, the reactant and at least one of the at least 2 electrodes wherein the one or more electrocatalytic properties are selected from at least one of electrical current, potential, charge, impedance, light, and color; and
   observing one or more electrocatalytic properties that are unique properties that correlate to a nanoparticles particle size.

2. The method of claim 1, wherein the oxidation or reduction reaction comprise an electrocatalytic amplification from a reduction reaction or an oxidation reaction catalyzed by the one or more nanoparticles.

3. The method of claim 1, wherein the one or more metal nanoparticles comprise platinum nanoparticles, gold nanoparticles, silver nanoparticles, copper nanoparticles, ruthenium nanoparticles, palladium nanoparticles, tin oxide nanoparticles, carbon nanoparticles or a combination thereof.

4. The method of claim 1, wherein the one or more electrocatalytic properties comprise a current, a resistance, an impedance, a capacitance, an inductance or a combination thereof.

5. The method of claim 1, wherein the one or more nanoparticles comprise platinum nanoparticles, gold nanoparticles, silver nanoparticles, copper nanoparticles, ruthenium nanoparticles, palladium nanoparticles, tin oxide nanoparticles, carbon nanoparticles or a combination thereof.

6. The method of claim 1, wherein the one or more nanoparticles are between 0.5 nm and 100 nm in diameter.

7. The method of claim 1, wherein the least 2 electrodes individually have a diameter of between about 1 µm and about 2 mm.

8. The method of claim 1, wherein the electrode has an area of between about 20 µm$^2$ and about 3 mm$^2$.

9. The method of claim 1, wherein the nanoparticle comprises at least 50 atoms of an element selected from gold, platinum, palladium, rhodium, copper, silver, ruthenium, iron, aluminum, nickel, and tin; and wherein the electrode comprises no more than a trace of said element.

10. The method of claim 1, further comprising at least one additional detector to form an array of detectors, wherein the array of detectors can detect individual nanoparticles at a plurality of electrodes.

11. The method of claim 1, wherein a rate of reaction attributable to the nanoparticle normalized to the nanoparticle's surface area is at least 10 times greater than a rate of reaction of the redox reactant attributable to the electrode normalized to the electrode's surface area.

12. The method of claim 1, wherein a rate of reaction attributable to the nanoparticle normalized to the nanoparticle's surface area is at least 10000 times greater than a rate of reaction of the redox reactant attributable to the electrode normalized to the electrode's surface area.

13. The method of claim 1, wherein the thin oxide film results in an inactive surface that allows electron tunneling.

14. An electrochemical cell to analyze a sample by electrocatalytic amplification using one or more nanoparticles comprising:
sodium borohydride (NaBH$_4$) as a heterogeneous inner sphere reductant,
one or more electrodes positioned to communicate with a sample housed within a sample chamber, wherein at least one of the one or more electrodes comprise a thin oxide film on the surface with a thickness that inhibits an inner sphere reaction of the one or more electrodes and allows collisions of one or more nanoparticles;
one or more nanoparticles deposited within the sample chamber, wherein the one or more nanoparticles interact with the sample, the thin oxide film and the one or more electrodes to generate one or more electrocatalytic properties, selected from electrical current, potential, charge, impedance, light, and color; and
a detector in communication with the one or more electrodes to detect the one or more electrocatalytic properties wherein the detector can detect through the thin oxide film individual nanoparticles contacting the electrode.

15. The electrochemical cell of claim 14, wherein the one or more electrodes comprise one or more ultramicroelectrodes.

16. The electrochemical cell of claim 14, wherein the one or more electrocatalytic properties comprise a current, a resistance, an impedance, a capacitance, an inductance or a combination thereof.

17. The electrochemical cell of claim 14, wherein the one or more electrocatalytic properties is an electrocatalytic amplification from a reduction reaction or an oxidation reaction catalyzed by the one or more nanoparticles.

18. The electrochemical cell of claim 14, wherein the one or metal nanoparticles comprise platinum nanoparticles, gold nanoparticles, silver nanoparticles, copper nanoparticles, ruthenium nanoparticles, palladium nanoparticles, tin oxide nanoparticles, carbon nanoparticles or a combination thereof.

19. The electrochemical cell of claim 14, wherein the one or more nanoparticles are between 0.5 nm and 100 nm in diameter.

20. A device having at least one nanoparticle for analyzing a chemical analyte comprising:
sodium borohydride (NaBH$_4$) as a heterogeneous inner sphere reductant,
an electrochemical cell comprising a container and at least 2 electrodes and a thin oxide film covering at least one of the at least 2 electrodes at a thickness that inhibits an inner sphere reaction and allows communication of one or more metal nanoparticles with the at least one of the at least 2 electrodes;
a solution comprising one or more chemical analytes and one or more metal nanoparticles in the container; and
a measuring apparatus connected to the at least 2 electrodes to detect one or more electrocatalytic properties generated by the one or more metal nanoparticles and the one or more chemical analytes at the at least one electrode.

21. The device of claim 20, wherein the one or more electrocatalytic properties is an electrocatalytic amplification from a reduction reaction or an oxidation reaction catalyzed by the one or more nanoparticles.

22. The device of claim 20, wherein the measuring apparatus detects electrical current; the one or more metal nanoparticles comprises at least 100 atoms of an element selected from gold, platinum, palladium, rhodium, carbon, and copper; the at least one electrode has an area ranging from about 20 µm$^2$ to 1 mm$^2$; and the nanoparticle ranges from 1 nm to 10 nm in diameter.

23. The device of claim 20, wherein the one or more nanoparticles comprise platinum nanoparticles, gold nanoparticles, silver nanoparticles, copper nanoparticles, ruthenium nanoparticles, palladium nanoparticles, tin oxide nanoparticles, carbon nanoparticles or a combination thereof.

* * * * *